(12) United States Patent
Getman

(10) Patent No.: US 10,961,594 B2
(45) Date of Patent: *Mar. 30, 2021

(54) COMPOSITIONS TO DETECT ATOPOBIUM VAGINAE NUCLEIC ACID

(71) Applicant: Gen-Probe Incorporated, San Diego, CA (US)

(72) Inventor: Damon K. Getman, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 23 days.

This patent is subject to a terminal disclaimer.

(21) Appl. No.: 16/156,100

(22) Filed: Oct. 10, 2018

(65) Prior Publication Data

US 2019/0024147 A1 Jan. 24, 2019

Related U.S. Application Data

(60) Division of application No. 14/925,812, filed on Oct. 28, 2015, now Pat. No. 10,138,525, which is a continuation of application No. 13/029,720, filed on Feb. 17, 2011, now Pat. No. 9,181,593, which is a continuation of application No. PCT/US2011/025215, filed on Feb. 17, 2011.

(60) Provisional application No. 61/305,319, filed on Feb. 17, 2010.

(51) Int. Cl.
*C12Q 1/689* (2018.01)
*C12Q 1/6865* (2018.01)

(52) U.S. Cl.
CPC ........... *C12Q 1/689* (2013.01); *C12Q 1/6865* (2013.01); *C12Q 2600/158* (2013.01)

(58) Field of Classification Search
None
See application file for complete search history.

(56) References Cited

U.S. PATENT DOCUMENTS

| | | |
|---|---|---|
| 5,654,418 A | 8/1997 | Sheiness et al. |
| 5,667,976 A | 9/1997 | Van Ness et al. |
| 5,700,636 A | 12/1997 | Sheiness et al. |
| 5,776,694 A | 7/1998 | Sheiness et al. |
| 6,107,033 A | 8/2000 | Welling et al. |
| 6,261,785 B1 | 7/2001 | Wood et al. |
| 7,303,870 B2 | 12/2007 | Hunter et al. |
| 7,625,704 B2 | 12/2009 | Fredricks et al. |
| 9,181,593 B2 | 11/2015 | Getman |
| 2003/0108921 A1 | 6/2003 | Jucker et al. |
| 2005/0130168 A1 | 6/2005 | Han et al. |
| 2006/0046246 A1 | 3/2006 | Zeng et al. |
| 2006/0172330 A1 | 8/2006 | Osborn et al. |
| 2007/0178495 A1 | 8/2007 | Fredricks et al. |
| 2007/0269813 A1 | 11/2007 | Dewhirst et al. |
| 2008/0038726 A1 | 2/2008 | Trama et al. |
| 2009/0291854 A1* | 11/2009 | Wiesinger-Mayr ......................... C12Q 1/6895 506/8 |
| 2010/0075306 A1 | 3/2010 | Bretelle et al. |
| 2017/0196914 A1 | 7/2017 | McKenzie et al. |

FOREIGN PATENT DOCUMENTS

| | | |
|---|---|---|
| WO | 2008003114 A2 | 1/2008 |
| WO | 2008062136 A2 | 5/2008 |

OTHER PUBLICATIONS

Backer et al., "Quantitative determination by real-time PCR of four vaginal *Lactobacillus* species, Gardnerella vaginalis and Atopobium vaginae indicates an inverse relationship between L. gasseri and L. iners," BMC Microbiology, Dec. 19, vol. 7, pp. 1-13. (Year: 2007).*
Biagi et al., "Quantitative variations in the vaginal bacterial population associated with asymptomatic infections: a real-time polymerase chain reaction study," Eur. J. Clin. Microbiol. Infect. Dis., 2008, Springer-Verlag, Berlin, Germany.
Boggess et al., "Use of DNA hybridization to detect vaginal pathogens associated with bacterial vaginosis among asymptomatic pregnant women," Am. J. Obstet. Gynecol., 2005,193:752-756, Elsevier Inc., New York, USA.
Bradshaw et al., "Evaluation of a Point-of-Care Test, BVBlue, and Clinical and Laboratory Criteria for Diagnosis of Bacterial Vaginosis," J. Clin. Microbiol., 2005, 43(3):1304-1308, American Society for Microbiology, Washington D.C., USA.
Bradshaw et al., "Higher-Risk Behavioral Practices Associated With Bacterial Vaginosis Compared with Vaginal Candidiasis," Obstet. Gynecol., 2005, 106(1):105-114, Lippincott Williams & Wilkins, Hagerstown, USA.
Bradshaw et al., "High Recurrence Rates of Bacterial Vaginosis over the Course of 12 Months after Oral Metronidazole Therapy and Factors Associated with Recurrence," J. Infec. Dis., 2006, 193:1478-1486, University of Chicago Press, Chicago, USA.
Bradshaw et al., "The Association of Atopobium vaginae and Gardnerella vaginalis with Bacterial Vaginosis and Recurrence after Oral Metronidazole Therapy," J. Infect. Dis., 2006, 194:828-836, Infectious Diseases Society of America, Chicago, USA.
Burton et al., "Evaluation of the Bacterial Vaginal Flora of 20 Postmenopausal Women by Direct (Nugent Score) and Molecular (Polymerase Chain Reaction and Denaturing Gradient Gel Electrophoresis) Techniques," J. Infec. Dis., 2002, 186:1770-1780, University of Chicago Press, Chicago, USA.

(Continued)

*Primary Examiner* — Young J Kim
(74) *Attorney, Agent, or Firm* — Nicholas V. Sherbina; Jeffrey E. Landes

(57) ABSTRACT

The disclosed invention include nucleic acid oligomers that may be used as amplification oligomers, including primers, as capture probes for sample preparation, and detection probes for detection of 16S rRNA from *Atopobium vaginae* in samples by using methods of specific nucleic acid amplification and detection.

18 Claims, 4 Drawing Sheets

Specification includes a Sequence Listing.

(56) References Cited

OTHER PUBLICATIONS

Burton et al., "Improved Understanding of the Bacterial Vaginal Microbiota of Women before and after Probiotic Instillation," Appl. Environ. Microbiol., 2003, 69(1):97-101, American Society for Microbiology, Washington D.C., USA.

Burton et al., "Detection of Atopobium vaginae in Postmenopausal Women by Cultivation-Independent Methods Warrants Further Investigation," J. Clin. Microbiol., 2004, 42(4):1829-1831, American Society for Microbiology, Washington D.C., USA.

Carr et al., "'Shotgun' Versus Sequential Testing: Cost-Effectiveness of Diagnostic Strategies for Vaginitis," J. Gen. Intern. Med., 2005, 20:793-799, Springer, Secaucus, Cohrssen et al., "Reliability of the Whiff Test in Clinical Practice," J. Am. Board Fam. Med., 2005, 561-562, American Board of Family Medicine, Lexington, USA.

Coolen et al., "Characterization of Microbial Communities Found in the Human Vagina by Analysis of Terminal Restriction Fragment Length Polymorphisms of 166 rRNA Genes," Appl. Environ. Microbiol., 2005, 71(12):8729-8737, American Society for Microbiology, Washington D.C., USA.

Deiman et al., "Characteristics and Applications of Nucleic Acid Sequence-Based Amplification (NASBA)," Molecular Biotechnology, 2002, 20:163-179, Humana Press, Inc., USA.

Devillard et al., "Novel insight into the vaginal microflora in postmenopausal women under hormone replacement therapy as analyzed by PCR-denaturing gradient gel electrophoresis," European Journal of Obstetrics & Gynecology and Reproductive Biology, 2004, 117:76-81, Elsevier, Limerick, Ireland.

Devillard et al., "Complexity of vaginal microflora as analyzed by PCR denaturing gradient gel eleotrophoresis in a patient with recurrent bacterial vaginosis," Infec. Dis. Obstet. Gynecol., 2005, 13(1):25-30, Wiley-Liss, New York, USA.

De Backer et al., "Quantitative determination by real-time PCR of four vaginal *Lactobacillus* species, Gardnerella vaginalis and Atopobium vaginae indicates an inverse relationship between L. gasseri and L. iners," BMC Microbiol., 2007, 7:115, BioMed Central, London, United Kingdom.

Dieffenbach et al., "General Concepts for PCR Primer Design," Genome Res., 1993,3:S30-S37, Cold Spring Harbor Laboratory.

Donders, "Diagnosis and Management of Bacterial Vaginosis and Other Types of Abnormal Vaginal Bacterial Flora: A Review," Obstetrical and Gynecological Survey, 2010, 65(7):462, Lippincott Williams & Wilkins, Hagerstown, USA.

Dumonceaux et al., "Multiplex Detection of Bacteria Associated with Normal Microbiota and with Bacterial Vaginosis in Vaginal Swabs by Use of Oligonucleotide-Coupled Fluorescent Microspheres," J. Clin. Microbiol., 2009, 47(12):4067-4077, American Society for Microbiology, Washington D.C., USA.

Eng, C., "Evaluation of Automated Transcription-Mediated Amplification Nucleic Acid Tests for Genitourinary Pathogens," 17th International Society for STD Research, 2007, Gen-Probe Incorporated, San Diego, 10210 Genetic Center Drive, San Diego, CA 92121.

Eschenbach, "History and Review Review of Bacterial Vaginosis," Am. J. Obstet. Gynecol., 1993, 169(2):441, Elsevier Inc., New York, USA.

Fan et al., "Human defensins and cytokines in vaginal ravage fluid of women with bacterial vaginosis," Int. J. Gynecol. Obstet., 2008, 103:50-54, Elsevier, Limerick, Ireland.

Ferris et al., "Association of Atopobium vaginae, a recently described metronidazole resistant anaerobe, with bacterial vaginosis," BMC Infectious Diseases, 2004, 4:5, BioMed Central, London, United Kingdom.

Ferris et al., "Use of Species-Directed 16S rRNA Gene PCR Primers for Detection of Atopobium Vaginae in Patients with Bacterial Vaginosis", Journals.ASM.org, J. Clin. Microbiol. 2004, 42(12):5892.

Forsum et al., "Bacterial vaginosis—a microbiological and immunological enigma," APMIS, 2005, 113:81-90, Munksgaard, Copenhagen, Denmark.

Fredricks et al., "Molecular Identification of Bacteria Associated with Bacterial Vaginosis," N. Engl. J. Med., 2005, 353:1899-1911, Massachusetts Medical Society, Boston, USA.

Fredricks et al., "Targeted Polymerase-Chain-Reaction for the Detection of Vaginal Bacteria Associated with Bacterial Vaginosis," J. Clin. Microbiol., 2007, pp. 1-25, American Society for Microbiology, Washington D.C., USA.

Fredricks et al., "Changes in Vaginal Bacterial Concentrations with Intravaginal Metronidazole Therapy for Bacterial Vaginosis as Assessed by Quantitative PCR," J. Clin. Microbiol., 2009, 47(3):721-726, American Society for Microbiology, Washington D.C., USA.

Gen Bank Accession No. AF325325.1 "Atopobium vaginae 16S ribosomal RNA gene, partial sequence—Nucleotide", Nov. 7, 2012, NCBI (www.ncbi.nlm.nih.gov/nuccore/AF325325).

Gunson et al., "Optimisation of PCR reactions using primer chessboarding," J. of Clinical Virology, 2003, 26:369-373, Elsevier Science B.V., UK.

Hale, "Correspondence: Bacteria Associated with Bacterial Vaginosis," N. Engl. J. Med., 2006, 354(2):202-203, Massachusetts Medical Society, Boston, USA.

Harmsen et al., "Development of 16S rRNA-Based Probes for the Coriobacterium Group and the Atopobium Cluster and Their Application for Enumeration of Coriobacteriaceae in Human Feces from Volunteers of Different Age Groups," Appl. Environ. Microbiol., 2000, 66(10):4523-4527, American Society for Microbiology, Washington D.C., USA.

Harwich et al., "Drawing the line between commensal and pathogenic Gardnerella vaginalis through genome analysis and virulence studies," BMC Genomics, 2010, 11:375, BioMed Central, London, United Kingdom.

Henriques et al., "In Silico vs in Vitro Analysis of Primer Specificity for the Detection of Gardnerella Vaginalis, Atopobium Vaginae and *Lactobacillus* Spp", BMC Research Notes, 2012, 5:637, http://www.biomedcentral.com/1756-0500/5/637.

Hill et al., "Extensive Profiling of a Complex Microbial Community by High-Throughput Sequencing," Appl. Environ. Microbiol., 2002, 68(6):3055-3066, American Society for Microbiology, Washington D.C., USA.

Hill et al., "Characterization of vaginal microflora of healthy, nonpregnant women by chaperonin-60 sequence-based methods," Am. J. Obstet. Gynecol., 2005, 193:682-692, Elsevier Inc., New York, USA.

Hilmarsdottir et al., "Evaluation of a Rapid Gram Stain Interpretation Method for Diagnosis of Bacterial Vaginosis," J. Clin. Microbiol., 2006, 44(3):1139-1140, American Society for Microbiology, Washington D.C., USA.

Hyman et al., "Microbes on the human vaginal epithelium" Proc. Natl. Acad. Sci. USA, 2005, 102(22):7952-7957, National Academy of Sciences, Washington D.C., USA.

Josey et al., "The polymicrobial hypothesis of bacterial vaginosis causation: a reassessment," Int. J. STD AIDS, 2008, 19:152-154, Royal Society of Medicine Services, London, United Kingdom.

Jovita et al., "Characterization of a novel Atopobium isolate from the human vagina: description of *Atopobium vaginae* sp. nov.," Int. J. Syst. Bacteriol., 1999, 49:1573-1576, Society for General Microbiology, Reading, United Kingdom.

Livengood, "Bacterial Vaginosis: An Overview for 2009," Rev. Obstet. Gynecol., 2009, 2(1):28-37, MedReviews LLC, New York, USA.

Marrazzo, "A Persistent(ly) Enigmatic Ecological Mystery: Bacterial Vaginosis," J. Infec. Dis., 2006, 193:1475-1477, University of Chicago Press, Chicago, USA.

Marrazzo et al., "Relationship of Specific Vaginal Bacteria and Bacterial Vaginosis Treatment Failure in Women who Have Sex with Women," Ann. Intern. Med., 2008, 149:20-28, American College of Physicians. Philadelphia, USA.

Matsuki et al., "Development of 168 rRNA-Gene-Targeted Group-Specific Primers for the Detection and Identification of Predominant Bacteria in Human Feces," Appl. Environ. Microbiol., 2002, 68(11):5445-5451, American Society for Microbiology, Washington D.C., USA.

(56) References Cited

OTHER PUBLICATIONS

Menard et al., "Molecular Quantification of Gardnerella vaginalis and Atopobium vaginae Loads to Predict Bacterial Vaginosis," Clin. Infec. Dis., 2008, 47:33-43, The University of Chicago Press, Chicago, USA.

Menard et al.,"High Vaginal Concentrations of Atopobium vaginae and Gardnerella vaginalis in Women Undergoing Preterm Labor," Obstet. Gynecol., 2010, 115(1):134-140, Lippincott Williams & Wilkins, Hagerstown, USA.

Nikolaitchouk et al., "The lower genital tract microblota in relation to cytokine-, SLPI- and endotoxin levels: application of checkerboard DNA-DNA hybridization (CDH)," APMIS, 2008, 116:263-277, Munksgaard, Copenhagen, Denmark.

Nugent et al., "Reliability of Diagnosing Bacterial Vaginosis is Improved by a Standardized Method of Gram Stain Interpretation," J. Clin. Microbiol., 1991, 29(2):297-301, American Society for Microbiology, Washington D.C., USA.

Nygren et al., "Evidence on the Benefits and Harms of Screening and Treating Pregnant Women Who Are Asymptomatic for Bacterial Vaginosis: An Update Review for the U.S. Preventive Services Task Force," Ann. Intern. Med., 2008, 148(3)220-233, American Society of Internal Medicine, Philadelphia, USA.

Oakley et al., "Diversity of Human Vaginal Bacterial Communities and Associations with Clinically Defined Bacterial Vaginosis," Appl. Environ. Microbiol., 2008, 74(15):4898-4909, American Society for Microbiology, Washington D. C., USA.

Persson et al., "The vaginal microflora in relation to gingivitis," BMC INfectious Diseases, 2009, 9:6, BioMed Central, London, United Kingdom.

Ravel et al., "Vaginal microbiome of reproductive-age women," Proc. Natl. Acad. Sci. USA, 2011, 108:4680-4687, National Academy of Sciences, Washington D.C., USA.

Ravel et al., Supporting Information to "Vaginal microbiome of reproductive-age women," 10.1073/pnas.1002611, http://www.pnas.org/cgi/content/short/1002611107, (2011).

Rinttila et al., "Development of an extensive set of 168 rDNA-targeted primers for quantification of pathogenic and indigenous bacteria in faecal samples by real-time PCR," Int. J. Appl. Microbiol., 2004, 97:1166-1177, The Society for Applied Microbiology, Oxford, United Kingdom.

Romanik, "Can Chlamydial Cervicitis Influence Diagnosis of Bacterial Vaginosis?" J. Clin. Microbiol., 2005, 43(9):4914-4915, American Society for Microbiology: Washington D.C., USA.

Rouse et al., "Diagnosis of bacterial vaginosis in the pregnant patient in an acute care setting," Arch. Gynecol. Obstet., 2008, Springer-Verlag, Berlin, Germany.

Roux, "Optimization and troubleshooting in PCR," Genome Res., 1995, 4:S185-S194, Cold Spring Harbor Laboratory Press, USA.

Rozen et al., "Primer3 on the WWW for General Users and for Biologist Programmers," Methods in Molecular Biology, 1999, 132:365-386, Humana Press Inc., USA.

Rychlik et al. , "A computer program for choosing optimal oligonucleotides for filter hybridization, sequencing and in vitro amplification of DNA," Nucleic Acids Res., 1989, 17(21):8543-8551, IRL Press, UK.

Schwiertz et al., "Throwing the dice for the diagnosis of vaginal complaints?" Ann. Clin. Microbiol. Antimicrob., 2006, 5:4, BioMed Cnetral, London, United Kingdom.

Sha et al., "Utility of Amsel Criteria, Nugent Score, and Quantitative PCR for Gardnerella vaginalis, Mycoplasma hominis, and *Lactobacillus* spp. for Diagnosis of Bacterial VAginosis in Human Immunodeficiency Virus-Infected Women," J. Clin. Microbiol., 2005, 43(9):4607-4612, American Society for Microbiology, Washington D.C., USA.

Spear et al., "Comparison of the Diversity of the Vaginal Microbiota in HIV-Infected and HIV-Uninfected Women with or without Bacterial Vaginosis," J. Infec. Dis., 2008, 198:1131-1140, University of Chicago Press, Chicago, USA.

Swidsinski et al., "Adherent Biofilms in Bacterial Vaginosis," Obstet. Gynecol., 2005, 106(5):1013-1023, Lippincott Williams & Wilkins, Hagerstown, USA.

Tabrizi et al., "Prevalence of Gardnerella vaginalis and Atopobium vaginae in Virginal Women," Sexually Transmitted Diseases, 2006, 33(11):663-665, American Sexually Transmitted Diseases Association.

Thies et al., "Rapid characterization of the normal and disturbed vaginal microbiota by application of 165 rRNA gene terminal RFLP fingerprinting," J. Med. Microbiol., 2007, 56:755-761, Society for General Microbiology, Reading, United Kingdom.

Trama et al., "Rapid detection of Atopoblum vaginae and association with organisms implicated in bacterial vaginosis," Mol. Cell. Probes, 2008, 22:96-102, Elsevier, New York, USA.

Vasquez et al., "Vaginal Lactobacillus Flora of Healthy Swedish Women," J. Clin. Microbiol., 2002, 40(8):2746-2749, American Society for Microbiology, Washington D.C., USA.

Van Der Pol, "Diagnosing Vaginal infections: It's Time to Join the 21st Century," Curr. Infec. Dis. Rep., 2010, Current Science, Philadelphia, USA.

Verhelst et al., "Cloning of 163 rRNA genes amplified from normal and disturbed vaginal microflora suggests a strong association between Atopobium vaginae, Gardnerella vaginalis and bacterial vaginosis," BMC Microbiol., 2004, 4(1):16, Blomed Central, London, Great Britain.

Verstraelen et al., "Culture-independent analysis of vaginal microflora: The unrecognized association of Atopobium vaginae with bacterial vaginosis," Am. J. Obstet. Gynecol., 2004, 191:1130-1132, Elsevier inc., New York, USA.

Vitali et al., "Dynamics of Vaginal Bacterial Communities in Women Developing Bacterial Vaginosis, Candidiasis, or No Infection, Analyzed by PCR-Denaturing Gradient Gel Electrophoresis and Real-Time PCR," Appl. Environ. Microbiol., 2007, 73(18):5731-5741, American Society for Microbiology, Washington D.C., USA.

Wu et al., The Effect ofTemperature and Oligonucleotide Primer Length on the Specificity and Efficiency of Amplification by the Polymerase Chain Reaction, 1991, DNA and Cell Biology, 10(3):233-238, Mary Ann Liebert, Inc. Publishers, USA.

Yudin et al., "Screening and Management of Bacterial Vaginosis in Pregnancy," Obstet. Gynaecol. Can., 2008, 211:702, Healthcare & Financial Pub., Rogers Media, Toronto, Canada.

Zhou et al., "Characterization of vaginal microbial communities in adult healthy women using cultivation-independent methods," Microbiology, 2004, 150:2565-2573, Society for General Microbiology, Reading, United Kingdom.

Zozaya-Hinchliffeet al., "Quantitative PCR Assessments of Bacterial Species in Women with and without Bacterial Vaginosis,"J. Clin. Microbiol., 2010, 48(5):1812-1819, American Society for Microbiology, Washington D.C., USA.

USPTO Non-Final Rejection, U.S. Appl. No. 13/029,720, dated Nov. 20, 2012.

USPTO Final Rejection, U.S. Appl. No. 13/029,720, dated Jan. 30, 2013.

USPTO Non-Final Rejection, U.S. Appl. No. 13/029,720, dated Oct. 6, 2014.

USPTO Interview Summary, U.S. Appl. No. 13/029,720, dated Jan. 22, 2015.

USPTO Final Rejection, U.S. Appl. No. 13/029,720, dated Mar. 31, 2015.

USPTO Notice Allowance and Examiner-Initiated Interview Summary, U.S. Appl. No. 13/029,720, dated Jul. 7, 2015.

USPTO Corrected Notice of Allowance, U.S. Appl. No. 13/029,720, dated Sep. 1, 2015.

USPTO Non Final Rejection, U.S. Appl. No. 14/925,812, dated Dec. 7, 2017.

USPTO Final Rejection, U.S. Appl. No. 14/925,812, dated Feb. 9, 2018.

USPTO Advisory Action, U.S. Appl. No. 14/925,812, dated Apr. 4, 20118.

USPTO Notice of Allowarice, U.S. Appl. No. 14/925,812, dated Jul. 27, 2018.

EPO Communication pursuant to Article 94(3), European Application No. 11705412.2, dated Feb. 21, 2014.

(56) References Cited

OTHER PUBLICATIONS

EPO Invitation pursuant to Article 94(3) and Rule 71(1) EPC, European Application No. 11745412.2, dated Mar. 13, 2015.
EPO Intention to Grant, European Application No. 11705412.2, dated Dec. 4, 2015.
EPO Decision to Grant, European Application No. 11705412.2, dated Apr. 4, 2016.
EPO Extended European Search Report, European Application No. 16153182.7, dated Jun. 1, 2016.
EPO Communication pursuant to Article 94(3) EPC, European Application No. 16153182.7, dated Sep. 19, 2017.
EPO Communication pursuant to Article 94(3) EPC, European Application No. 16153182.7, dated May 11, 2018.
PCT International Preliminary Report on Patentability, International Application No. PCT/US2011/025215, dated Aug. 21, 2012.
PCT International Search Report, International Application No. PCT/US2011/025215, dated Jun. 10, 2011.
PCT Written Opinion, International Application No. PCT/US2011/025215, dated Jun. 10, 2011.
OSOM BVBLUE Test, Sekisui Diagnostics, LLC, San Diego, CA, Catalogue #183, http://www.sekisuidiagnostics.com/pdf/OSOM_BVBLUE_183_PI.pdf (Oct. 2009).

\* cited by examiner gatgaacgctggcggcgcgcctaacacatgcaagtcgaacggttaaa
gcatcttcggatgtgtataaagtggcgaacggctgagtaacacgtgg
gcaacctgcccttttgcactgggatagcctcgggaaaccgaggttaat
accggatactccatatttgtcgcatggcgaatatgggaaagctccgg
cggcaaaggatgggcccgcggcctgttagctagttggtggggtagtg
gcctaccaaggcaatgatgggtagccggttgagagaccgaccggcc
agattgggactgagacacggcccagactcctacgggaggcagcagtg
gggaatcttgcacaatgggcgaaagcctgatgcagcgacgccgcgtg
cgggatgaaggccttcgggttgtaaaccgctttcagcagggacgagg
ccgcaaggtgacggtacctgcagaagaagccccggctaactacgtgc
cagcagccgcggtaatacgtaggggcaagcgttatccggattcatt
gggcgtaaagcgcgcgtaggcggtctgttaggtcaggagttaaatct
ggggctcaaccctatccgctcctgataccggcaggcttgagtctg
gtaggggaagatggaattccaagtgtagcggtgaaatgcgcagatat
ttggaagaacaccggtggcgaaggcggtcttctgggccatgactgac
gctgaggcgcgaaagctaggggagcgaacaggattagataccctggt
agtcctagctgtaaacgatggacactaggtgtggggagattatactt
tccgtgccgcagctaacgcattaagtgtcccgcctggggagtacggt
cgcaagactaaaactcaaaggaattgacgggggcccgcacaagcagc
ggagcatgtggcttaattcgaagcaacgcgaagaaccttaccagggc
ttgacatttaggtgaagcagtggaaacactgtggccgaaaggagcct
aaacaggtggtgcatggctgtcgtcagctcgtgtcgtgagatgttgg
gttaagtcccgcaacgagcgcaacccttgtcgcatgttgccagcggt
tcggccgggcacccatgcgagaccgccggcgttaagccggaggaagg
tggggacgacgtcaagtcatcatgccccttatgtcctgggctgcaca
cgtgctacaatggccggcacagagggctgctactgcgcgagcagaag
cgaatccctaaagccggtcccagttcggattggagctgcaactcgc
ctccatgaagtcggagttgctagtaatcgcggatcagcacgccgcgg
tgaatgcgttcccgggccttgtacacaccgcccgtcacaccacccga
gtcgtctgcaccgaagtcgtcggcctaacccgcaagggagggaggc
gccgaaggtgtggagggtaagggggt

SEQ ID NO:1

Fig.1

```
                   410        420        430        440        450
            ....|....|....|....|....|....|....|....|....|....|
SID # 2     -----CTTTCAGCAGGGACGAGG---------------------------
SID # 27    --------------------------------------------------
SID # 1     AACCGCTTTCAGCAGGGACGAGGCCGCAAGGTGACGGTACCTGCAGAAGA 460        470        480        490        500
            ....|....|....|....|....|....|....|....|....|....|
SID # 2     --------------------------------------------------
SID # 27    --------------------------------------------------
SID # 1     AGCCCCGGCTAACTACGTGCCAGCAGCCGCGGTAATACGTAGGGGGCAAG 510        520        530        540        550
            ....|....|....|....|....|....|....|....|....|....|
SID # 2     --------------------------------------------------
SID # 27    --------------------------------------------------
SID # 1     CGTTATCCGGATTCATTGGGCGTAAAGCGCGCGTAGGCGGTCTGTTAGGT 560        570        580        590        600
            ....|....|....|....|....|....|....|....|....|....|
SID # 2     --------------------------------------------------
SID # 27    --------------------TCAACCCCTATCCGCTCCTGATA-------
SID # 1     CAGGAGTTAAATCTGGGGGCTCAACCCCTATCCGCTCCTGATACCGGCAG
```

FIG.2A

```
                  410       420       430       440       450
             ....|....|....|....|....|....|....|....|....|....|
SID # 2      -----CTTTCAGCAGGGACGAGG---------------------------
SID # 27     --------------------------------------------------
SID # 43     -----CTTTCAGCAGGGACGAGGCCGCAAGGTGACGGTACCTGCAGAAGA 460       470       480       490       500
             ....|....|....|....|....|....|....|....|....|....|
SID # 2      --------------------------------------------------
SID # 27     --------------------------------------------------
SID # 43     AGCCCCGGCTAACTACGTGCCAGCAGCCGCGGTAATACGTAGGGGGCAAG 510       520       530       540       550
             ....|....|....|....|....|....|....|....|....|....|
SID # 2      --------------------------------------------------
SID # 27     --------------------------------------------------
SID # 43     CGTTATCCGGATTCATTGGGCGTAAAGCGCGCGTAGGCGGTCTGTTAGGT 560       570       580       590       600
             ....|....|....|....|....|....|....|....|....|....|
SID # 2      --------------------------------------------------
SID # 27     --------------------TCAACCCCTATCCGCTCCTGATA-------
SID # 43     CAGGAGTTAAATCTGGGGGCTCAACCCCTATCCGCTCCTGATA-------
```

FIG.2B

```
              410       420       430       440       450
         ....|....|....|....|....|....|....|....|....|....|
SID#4    --------------------------------------------------
SID#15   --------------------------------------------------
SID#16   --------------------------------------------------
SID#17   --------------------------------------------------
SID#43   -----CTTTCAGCAGGGACGAGGCCGCAAGGTGACGGTACCTGCAGAAGA
SID#1    AACCGCTTTCAGCAGGGACGAGGCCGCAAGGTGACGGTACCTGCAGAAGA 460       470       480       490       500
         ....|....|....|....|....|....|....|....|....|....|
SID#4    --------------------------------------------------
SID#15   --------------------------------------------------
SID#16   --------------------------------------------------
SID#17   --------------------------------------------------
SID#43   AGCCCCGGCTAACTACGTGCCAGCAGCCGCGGTAATACGTAGGGGGCAAG
SID#1    AGCCCCGGCTAACTACGTGCCAGCAGCCGCGGTAATACGTAGGGGGCAAG 510       520       530       540       550
         ....|....|....|....|....|....|....|....|....|....|
SID#4    -----------------------------------------------GGU
SID#15   ---------------------------------------------GTTAGGT
SID#16   -----------------------------------------CGGTCTGTTAGGT
SID#17   -----------------------------------------------GGT
SID#43   CGTTATCCGGATTCATTGGGCGTAAAGCGCGCGTAGGCGGTCTGTTAGGT
SID#1    CGTTATCCGGATTCATTGGGCGTAAAGCGCGCGTAGGCGGTCTGTTAGGT 560       570       580       590       600
         ....|....|....|....|....|....|....|....|....|....|
SID#4    CAGGAGUUAAAUCUGG----------------------------------
SID#15   CAGGAGTTAAATCTGG----------------------------------
SID#16   CAGGAGTT------------------------------------------
SID#17   CAGGAGTTAAATCTGG----------------------------------
SID#43   CAGGAGTTAAATCTGGGGGCTCAACCCCTATCCGCTCCTGATA-------
SID#1    CAGGAGTTAAATCTGGGGGCTCAACCCCTATCCGCTCCTGATACCGGCAG
```

Fig.2C

SEQUENCE LISTING

<160> NUMBER OF SEQ ID NOS: 57

<210> SEQ ID NO 1
<211> LENGTH: 1437
<212> TYPE: DNA
<213> ORGANISM: Artificial Sequence
<220> FEATURE:
<223> OTHER INFORMATION: Atopobium Vaginae.  GenBank No. AF 325325.1 gi: 12240234 (Jan. 16, 2001)

<400> SEQUENCE: 1

```
gatgaacgct ggcggcgcgc ctaacacatg caagtcgaac ggttaaagca tcttcggatg    60
tgtataaagt ggcgaacggc tgagtaacac gtgggcaacc tgcccttgc actgggatag    120
cctcgggaaa ccgaggttaa taccggatac tccatatttg tcgcatggcg aatatgggaa    180
agctccggcg gcaaaggatg ggcccgcggc ctgttagcta gttggtgggg tagtggccta    240
ccaaggcaat gatgggtagc cgggttgaga gaccgaccgg ccagattggg actgagacac    300
ggcccagact cctacgggag gcagcagtgg ggaatcttgc acaatgggcg aaagcctgat    360
gcagcgacgc cgcgtgcggg atgaaggcct tcgggttgta accgctttc agcagggacg    420
aggccgcaag gtgacggtac tgcagaagaa gccccggct aactacgtgc cagcagccgc    480
ggtaatacgt aggggggcaag cgttatccgg attcattggg cgtaaagcgc gcgtaggcgg    540
tctgttaggt caggagttaa atctgggggc tcaaccccta tccgctcctg ataccggcag    600
gcttgagtct ggtaggggaa gatggaattc caagtgtagc ggtgaaatgc gcagatattt    660
ggaagaacac cggtggcgaa ggcggtcttc tgggccatga ctgacgctga ggcgcgaaag    720
ctaggggagc gaacaggatt agataccctg gtagtcctag ctgtaaacga tggacactag    780
gtgtggggag attatacttt ccgtgccgca gctaacgcat taagtgtccc gcctggggag    840
tacggtcgca agactaaaac tcaaaggaat tgacggggc ccgcacaagc agcggagcat    900
gtggcttaat tcgaagcaac gcgaagaacc ttaccagggc ttgacattta ggtgaagcag    960
tggaaacact gtggccgaaa ggagcctaaa caggtggtgc atggctgtcg tcagctcgtg    1020
tcgtgagatg ttgggttaag tcccgcaacg agcgcaaccc ttgtcgcatg ttgccagcgg    1080
ttcggccggg cacccatgcg agaccgccgg cgttaagccg gaggaaggtg gggacgacgt    1140
caagtcatca tgccccttat gtcctgggct gcacacgtgc tacaatggcc ggcacagagg    1200
gctgctactg cgcgagcaga agcgaatccc taaagccggt cccagttcgg attggaggct    1260
gcaactcgcc tccatgaagt cggagttgct agtaatcgcg gatcagcacg ccgcggtgaa    1320
tgcgttcccg ggccttgtac acaccgcccg tcacaccacc cgagtcgtct gcacccgaag    1380
tcgtcggcct aacccgcaag ggagggaggc gccgaaggtg tgagggtaa gggggt        1437
```

<210> SEQ ID NO 2
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 2

```
ctttcagcag ggacgagg                                                    18
```

<210> SEQ ID NO 3
<211> LENGTH: 50
<212> TYPE: DNA
<213> ORGANISM: Artificial Sequence
<220> FEATURE:

```
<223> OTHER INFORMATION: Synthetic Oligomer
<220> FEATURE:
<221> NAME/KEY: promoter
<222> LOCATION: (1)..(27)

<400> SEQUENCE: 3
aatttaatac gactcactat agggagatat caggagcgga tagggttga         50

<210> SEQ ID NO 4
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 4
ggucaggagu uaaaucugg                                          19

<210> SEQ ID NO 5
<211> LENGTH: 55
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (23)..(55)
<223> OTHER INFORMATION: dT3/dA30 tail

<400> SEQUENCE: 5
ctactgctgc ctcccgtagg agtttaaaaa aaaaaaaaaa aaaaaaaaaa aaaaa   55

<210> SEQ ID NO 6
<211> LENGTH: 57
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (25)..(57)
<223> OTHER INFORMATION: dT3/dA30 tail

<400> SEQUENCE: 6
ggactaccag ggtatctaat cctgtttaaa aaaaaaaaaa aaaaaaaaaa aaaaaaa 57

<210> SEQ ID NO 7
<211> LENGTH: 59
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (27)..(59)
<223> OTHER INFORMATION: dT3/dA30 tail

<400> SEQUENCE: 7
cgacacgagc tgacgacagc catgcattta aaaaaaaaaa aaaaaaaaaa aaaaaaaaa 59

<210> SEQ ID NO 8
<211> LENGTH: 53
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (21)..(53)
```

```
<223> OTHER INFORMATION: dT3/dA30 tail

<400> SEQUENCE: 8
gacgtcatcc ccaccttcct tttaaaaaaa aaaaaaaaaa aaaaaaaaaa aaa        53

<210> SEQ ID NO 9
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 9
ggattagata ccctggtagt cc                                          22

<210> SEQ ID NO 10
<211> LENGTH: 45
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 10
aatttaatac gactcactat agggagaccc gtcaattcct ttgag                 45

<210> SEQ ID NO 11
<211> LENGTH: 31
<212> TYPE: DNA
<213> ORGANISM: Artificial Sequence
<220> FEATURE:
<223> OTHER INFORMATION: Synthetic Oligomer

<400> SEQUENCE: 11
actgagacac ggcccaaact cctacgggag g                                31

<210> SEQ ID NO 12
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 12
actcctacgg gaggcagcag tag                                         23

<210> SEQ ID NO 13
<211> LENGTH: 47
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 13
aatttaatac gactcactat agggagatta ccgcggctgc tggcacg               47

<210> SEQ ID NO 14
<211> LENGTH: 26
<212> TYPE: DNA
<213> ORGANISM: Artificial Sequence
<220> FEATURE:
<223> OTHER INFORMATION: Synthetic Oligomer
```

<400> SEQUENCE: 14
tcagcaggga cgaggccgca aggtga                                                26

<210> SEQ ID NO 15
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 15
gttaggtcag gagttaaatc tgg                                                   23

<210> SEQ ID NO 16
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 16
cggtctgtta ggtcaggagt t                                                     21

<210> SEQ ID NO 17
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 17
ggtcaggagt taaatctgg                                                        19

<210> SEQ ID NO 18
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 18
ccgaggttaa taccggatac tc                                                    22

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 19
aagtggcgaa cggctgagta a                                                     21

<210> SEQ ID NO 20
<211> LENGTH: 46
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 20
aatttaatac gactcactat agggagaatc attgccttgg taggcc           46

<210> SEQ ID NO 21
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 21
ctactgctgc ctcccgtagg ag                                              22

<210> SEQ ID NO 22
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 22
ggactaccag ggtatctaat cctg                                            24

<210> SEQ ID NO 23
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 23
cgacacgagc tgacgacagc catgca                                          26

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 24
gacgtcatcc ccaccttcct                                                 20

<210> SEQ ID NO 25
<211> LENGTH: 27
<212> TYPE: DNA
<213> ORGANISM: Artificial Sequence
<220> FEATURE:
<223> OTHER INFORMATION: Synthetic Oligomer: T7 Promoter Sequence

<400> SEQUENCE: 25
aatttaatac gactcactat agggaga                                         27

<210> SEQ ID NO 26
<211> LENGTH: 42
<212> TYPE: DNA
<213> ORGANISM: Artificial Sequence
<220> FEATURE:
<223> OTHER INFORMATION: Synthetic Oligomer

<400> SEQUENCE: 26
ctttcagcag ggacgaggct caacccctat ccgctcctga ta                        42

<210> SEQ ID NO 27
<211> LENGTH: 23
<212> TYPE: DNA
<213> ORGANISM: Artificial Sequence
<220> FEATURE:

```
<223> OTHER INFORMATION: Synthetic Oligomer

<400> SEQUENCE: 27
tatcaggagc ggatagggt tga                                          23

<210> SEQ ID NO 28
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 28
cccgtcaatt cctttgag                                               18

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 29
ttaccgcggc tgctggcacg                                             20

<210> SEQ ID NO 30
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 30
atcattgcct tggtaggcc                                              19

<210> SEQ ID NO 31
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 31
gtggcgaacg gctgagtaac ac                                          22

<210> SEQ ID NO 32
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 32
aacggctgag taacacgtg                                              19

<210> SEQ ID NO 33
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 33
ggcaacctgc cctttgcact gggata                                      26
```

<210> SEQ ID NO 34
<211> LENGTH: 28
<212> TYPE: DNA
<213> ORGANISM: Artificial Sequence
<220> FEATURE:
<223> OTHER INFORMATION: Synthetic Oligomer

<400> SEQUENCE: 34
tgcccttcgc actgggatag cctcggga                                    28

<210> SEQ ID NO 35
<211> LENGTH: 50
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 35
aatttaatac gactcactat agggagagga gtatccggta ttaacctcgg            50

<210> SEQ ID NO 36
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 36
ggagtatccg gtattaacct cgg                                         23

<210> SEQ ID NO 37
<211> LENGTH: 48
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 37
aatttaatac gactcactat agggagagga gtatccggta ttaacctc              48

<210> SEQ ID NO 38
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 38
ggagtatccg gtattaacct c                                           21

<210> SEQ ID NO 39
<211> LENGTH: 52
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (20)..(52)
<223> OTHER INFORMATION: dT3/dA30 tail

<400> SEQUENCE: 39

```
ccaccaacta gctaacaggt ttaaaaaaaa aaaaaaaaa aaaaaaaaa aa              52

<210> SEQ ID NO 40
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 40
ccaccaacta gctaacagg                                                 19

<210> SEQ ID NO 41
<211> LENGTH: 59
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (27)..(59)
<223> OTHER INFORMATION: dT3/dA30 tail

<400> SEQUENCE: 41
aacccggcta cccatcattg ccttggttta aaaaaaaaa aaaaaaaaa aaaaaaaa        59

<210> SEQ ID NO 42
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 42
aacccggcta cccatcattg ccttgg                                         26

<210> SEQ ID NO 43
<211> LENGTH: 188
<212> TYPE: DNA
<213> ORGANISM: Artificial Sequence
<220> FEATURE:
<223> OTHER INFORMATION: Exemplary Amplicon's Target Specific Sequence

<400> SEQUENCE: 43
ctttcagcag ggacgaggcc gcaaggtgac ggtacctgca gaagaagccc cggctaacta    60
cgtgccagca gccgcggtaa tacgtagggg gcaagcgtta tccggattca ttgggcgtaa   120
agcgcgcgta ggcggtctgt taggtcagga gttaaatctg ggggctcaac ccctatccgc   180
tcctgata                                                            188

<210> SEQ ID NO 44
<211> LENGTH: 29
<212> TYPE: DNA
<213> ORGANISM: Artificial Sequence
<220> FEATURE:
<223> OTHER INFORMATION: Synthetic Oligomer or Residues 538 to 566 of AF
      325325.1 gi: 12240234 (Jan. 16, 2001)

<400> SEQUENCE: 44
cggtctgtta ggtcaggagt taaatctgg                                      29

<210> SEQ ID NO 45
<211> LENGTH: 23
<212> TYPE: DNA
<213> ORGANISM: Artificial Sequence
<220> FEATURE:
```

<223> OTHER INFORMATION: Synthetic Oligomer or Residues 544 to 566 of AF
      325325.1 gi: 12240234 (Jan. 16, 2001)

<400> SEQUENCE: 45
gttaggtcag gagttaaatc tgg                                          23

<210> SEQ ID NO 46
<211> LENGTH: 19
<212> TYPE: DNA
<213> ORGANISM: Artificial Sequence
<220> FEATURE:
<223> OTHER INFORMATION: Synthetic Oligomer or Residues 548 to 566 of AF
      325325.1 gi: 12240234 (Jan. 16, 2001)

<400> SEQUENCE: 46
ggtcaggagt taaatctgg                                               19

<210> SEQ ID NO 47
<211> LENGTH: 21
<212> TYPE: DNA
<213> ORGANISM: Artificial Sequence
<220> FEATURE:
<223> OTHER INFORMATION: Synthetic Oligomer or Residues 538 to 558 of AF
      325325.1 gi: 12240234 (Jan. 16, 2001)

<400> SEQUENCE: 47
cggtctgtta ggtcaggagt t                                            21

<210> SEQ ID NO 48
<211> LENGTH: 11
<212> TYPE: DNA
<213> ORGANISM: Artificial Sequence
<220> FEATURE:
<223> OTHER INFORMATION: Synthetic Oligomer or Residues 548 to 558 of AF
      325325.1 gi: 12240234 (Jan. 16, 2001)

<400> SEQUENCE: 48
ggtcaggagt t                                                       11

<210> SEQ ID NO 49
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 49
ccugutttuu ctcctgucc                                               19

<210> SEQ ID NO 50
<211> LENGTH: 29
<212> TYPE: DNA
<213> ORGANISM: Artificial Sequence
<220> FEATURE:
<223> OTHER INFORMATION: synthetic oligomer or residues 406 to 434 of
      GenBank Accession Number AF325325.1, gi:12240234 (Jan 16, 2001)

<400> SEQUENCE: 50
ctttcagcag ggacgaggcc gcaaggtga                                    29

<210> SEQ ID NO 51
<211> LENGTH: 26
<212> TYPE: DNA
<213> ORGANISM: artificial sequence
<220> FEATURE:
<223> OTHER INFORMATION: synthetic oligomer

```
<400> SEQUENCE: 51
tcaccttgcg gcctcgtccc tgctga                                          26

<210> SEQ ID NO 52
<211> LENGTH: 23
<212> TYPE: DNA
<213> ORGANISM: Artificial Sequence
<220> FEATURE:
<223> OTHER INFORMATION: synthetic oligomer

<400> SEQUENCE: 52
ccagatttaa ctcctgacct aac                                             23

<210> SEQ ID NO 53
<211> LENGTH: 21
<212> TYPE: DNA
<213> ORGANISM: Artificial Sequence
<220> FEATURE:
<223> OTHER INFORMATION: synthetic oligomer

<400> SEQUENCE: 53
aactcctgac ctaacagacc g                                               21

<210> SEQ ID NO 54
<211> LENGTH: 19
<212> TYPE: DNA
<213> ORGANISM: Artificial Sequence
<220> FEATURE:
<223> OTHER INFORMATION: synthetic oligomer

<400> SEQUENCE: 54
ccagatttaa ctcctgacc                                                  19

<210> SEQ ID NO 55
<211> LENGTH: 22
<212> TYPE: DNA
<213> ORGANISM: Artificial Sequence
<220> FEATURE:
<223> OTHER INFORMATION: synthetic oligomer

<400> SEQUENCE: 55
gagtatccgg tattaacctc gg                                              22

<210> SEQ ID NO 56
<211> LENGTH: 26
<212> TYPE: DNA
<213> ORGANISM: Artificial Sequence
<220> FEATURE:
<223> OTHER INFORMATION: synthetic oligomer

<400> SEQUENCE: 56
tatcccagtg caaagggcag gttgcc                                          26

<210> SEQ ID NO 57
<211> LENGTH: 28
<212> TYPE: DNA
<213> ORGANISM: Artificial Sequence
<220> FEATURE:
<223> OTHER INFORMATION: synthetic oligomer

<400> SEQUENCE: 57
tcccgaggct atcccagtgc aaagggca                                        28
```

COMPOSITIONS TO DETECT ATOPOBIUM VAGINAE NUCLEIC ACID

RELATED APPLICATIONS

This Application is a divisional of U.S. application Ser. No. 14/925,812, which was filed on Oct. 28, 2015, now allowed, which is a continuation of U.S. application Ser. No. 13/029,720, which was filed on Feb. 17, 2011, now issued as U.S. Pat. No. 9,181,593, which claims priority to U.S. Provisional Application No. 61/305,319, which was filed on Feb. 17, 2010, and to International Application PCT/US11/25215, which was filed on Feb. 17, 2011. The contents of each of the foregoing applications are incorporated by reference herein in their entirety.

REFERENCE TO SEQUENCE LISTING

The instant application contains a Sequence Listing which has been submitted in ASCII format via EFS-Web and is hereby incorporated by reference in its entirety. Said ASCII Copy, created on Oct. 8, 2018, is named "GP232_03UT_ST25" and is 14,578 bytes in size.

FIELD OF THE INVENTION

This invention relates to detection of the presence of *Atopobium* bacteria in a sample by using molecular biological methods, and specifically relates to detection of *Atopobium vaginae* in a sample by amplifying nucleic acids from *Atopobium vaginae* and detecting the amplified nucleic acid sequences.

BACKGROUND

*Atopobium vaginae* ("*A. vaginae*") are a species of the *Atopobium* genus of bacteria. This strain was first described by Rodriguez et al. (Int. J. Syst. Bacteriol. (1999) 49:1573-1576) having been identified from the vaginal flora of a health individual. *A. vaginae* has since been implicated in bacterial vaginosis, wherein the *A. vaginae* load increases relative to other species of the natural flora. (Ferris, M., et al., BMC Infect. Dis. (2004) 4:5. Verhelst, R., et al., BMC Microbiol. (2004) 4:16). Bacterial vaginosis (BV) is a poorly detected public health problem that is associated with increased susceptibility to sexually transmitted disease, pre-term delivery, pelvic inflammatory disease, neoplasia and low birth weight and for which no reliable diagnostic tool exists.

Bacterial vaginosis is currently considered to be a synergistic polymicrobial syndrome that is characterized by depletion of *Lactobacillus* spp., especially those that produce hydrogen peroxide, and an intense increase (100- to 1000-fold above normal levels) in the quantity of commensal vaginal anaerobic bacteria, including *G. vaginalis*, *Prevotella* sp, anaerobic gram positive cocci, *Mobiluncus* sp, *Mycoplasma hominis*, *Eggerthella* hongkongensis, *Megasphaera* sp, *Leptotrichia sanguinegens* and *Atopobium vaginalis*. (See, e.g., Swidsinksi, et al., Obstet. Gynecol. (2005) 106:1013; see also, Thies et al., J. Medical Microbiol., (2007) 56, 755.) Diagnosing of bacterial vaginosis, therefore, requires identifying each microbe present in the vaginal flora and determining their relative abundances within the floral population.

A current technique for diagnosing BV includes gram-staining assays; however, gram-staining techniques are less than optimal. One particular problem is that *A. vaginae* present a variable morphology that hinders identification using gram-staining. (Menard et al. Clin Infect Dis. (2008) 47(1):33-43). Nucleic acid diagnostic tests marketed for identifying BV pathogens lack components for identifying *A. vaginae*. (BD Affirm VPIII, Becton Dickinson, Sparks, Md.). Other nucleic acid tests rely upon universal primers and probes that detect a plurality of microbes identified in normal and disease state flora. Universal flora detection tests are known to provide confounding and incomplete results due to competition by abundant flora masking the presence of less abundant flora. Thus, results from these diagnostic assays are not fully indicative of what is occurring in a BV infection, particularly by failing to indicate the presence or abundance of *A. vaginae* in a specimen. There is a need for compositions, kits and methods that allow rapid and accurate diagnosis of BV, wherein said compositions, kits and methods detect the presence or abundance of *A. vaginae* in a specimen so that individuals may be promptly and properly treated to prevent complications from the disorder. There is also a need wherein said compositions, kits and methods detect the presence or relative abundance of *A. vaginae* in a specimen so that individuals may be promptly and properly treated to prevent complications from the disorder. There is also a need wherein said compositions, kits and methods detect the presence or relative abundance of each of a plurality of microbes in a specimen so that individuals may be promptly and properly treated to prevent complications from the disorder.

SUMMARY

The present invention relates to compositions, kits, and methods used in detecting *Atopobium vaginae*. The invention is based at least in part on the discovery that certain *A. vaginae* sequences are surprisingly efficacious for the detection of *A. vaginae*. In certain aspects and embodiments, particular regions of the *A. vaginae* 16S rRNA have been identified as preferred targets for nucleic acid amplification reactions of a sample, including biological specimens derived from infected humans. In certain aspects and embodiments, particular regions of the *A. vaginae* 16S rRNA have been identified as preferred targets for nucleic acid detection reactions of a sample, including biological specimens derived from infected humans, and amplifications products therefrom. These preferred target regions provide improvements in relation to specificity, sensitivity, or speed of detection as well as other advantages. The invention also includes nucleic acid oligomers that may be used as primers and probes for detecting *A. vaginae*, and which may be provided in kits. Using the specific primers and probes, the methods include one or more of the steps of isolating/capturing target nucleic acids from a sample, amplifying target sequences within the 16S rRNA nucleic acid of *A. vaginae* and detecting the amplification products. Some embodiments of the methods monitor the development of specific amplification products during the amplification step. Preferred compositions of the instant invention are configured to specifically hybridize to a 16S rRNA nucleic acid of *A. vaginae* with minimal cross-reactivity to other nucleic acids suspected of being in a sample. In some aspects, the compositions of the instant invention are configured to specifically hybridize to a 16S rRNA nucleic acid of *A. vaginae* with minimal cross-reactivity to one or more of anaerobic gram-positive cocci; *Megasphaera* sp.; *Lactobacillus* sp.; *Lactobacillus iners*; *Lactobacillus crispatus* group; *Lactobacillus gasseri* group; *Gardnerella* sp; *Gardnerella vaginalis*; *Trichamonas* sp; *Trichamonas vaginalis*;

*Candida* sp; *Eggerthella* sp.; *Bacterium* from the order Clostridiales; *Clostridium*-like sp.; *Prevotella* sp.; *Prevotella bivia* group; *Prevotella buccalis* group; *Atopobium* sp.; *Atopobium vaginae*; Enterobacteria; *Peptostreptococcus micros*; *Aerococcus christensenii*; *Leptotrichia amnionii*; *Peptoniphilus* sp.; *Dialister* sp.; *Mycoplasma hominis*; *Sneathia sanguinegens*; *Anaerococcus tetradius*; *Mobiluncus* sp.; *Mobiluncus hominis*; *Eggerthella hongkongensis*; *Megasphaera* sp; *Leptotrichia sanguinegens* and *Finegoldia magna*. In one aspect, the compositions of the instant invention are part of a multiplex system that further includes components and methods for detecting one of more of these organisms.

One aspect of the invention includes compositions for detecting *A. vaginae* in a sample. Preferred embodiments include combinations of nucleic acid oligomers that function as amplification oligonucleotides in nucleic acid amplification reactions, and probes that hybridize specifically to amplified nucleic acid products, or directly to the 16S rRNA or a gene that encodes the 16S rRNA of *A. vaginae*. Some embodiments are kits that contain such amplification oligonucleotides and/or probes specific for target *A. vaginae* nucleic acid, and which may optionally include other reagents used in nucleic acid amplification and/or detection.

One embodiment of compositions for the amplification and detection of *A. vaginae* target nucleic acids includes amplification oligomers. A preferred embodiment of amplification oligomers for amplifying a 16S rRNA of *A. vaginae* or a gene encoding a 16S rRNA of *A. vaginae*, are amplification oligomers configured to generate an amplicon comprising a target specific sequence that is from about 150 nucleotides in length to about 235 nucleotides in length and that is at least 80% identical to SEQ ID NO:43. More preferably, the amplification oligomers are configured to generate an amplicon that comprises a target specific sequence that is from about 169 nucleotides in length to about 209 nucleotides in length and that is at least 90% identical to SEQ ID NO:43. More preferably still, the amplification oligomers are configured to generate an amplicon that comprises a target specific sequence that is from about 178 nucleotides in length to about 198 nucleotides in length and is at least 95% identical to SEQ ID NO:43. And still more preferably, the amplification oligomers are configured to generate an amplicon that comprises a target specific sequence that is SEQ ID NO:43. Ranges for the length of a nucleic acid are inclusive of all whole numbers therein. Ranges for percent identity are inclusive of all whole and partial numbers therein.

In a preferred embodiment, the amplification oligomers comprise an oligomer member that is SEQ ID NO:2. In a preferred embodiment, the amplification oligomers comprise an oligomer member that is SEQ ID NO:27. In a preferred embodiment, the amplification oligomers comprise first and second oligomer members that are SEQ ID NO:2 and SEQ ID NO:27. In a preferred embodiment, the amplification oligomers comprise an oligomer member with a target binding sequence that is SEQ ID NO:27. In a preferred embodiment, the amplification oligomers comprise a first oligomer member that is SEQ ID NO:2 and a second oligomer member with a target binding sequence that is SEQ ID NO:27.

In an alternatively preferred embodiment, the amplification oligomers comprise an oligomer member that further comprises a promoter sequence attached to the oligomer member's 5' end. Preferably, the amplification oligomers comprise an oligomer member that is SEQ ID NO:27, which further comprises a promoter sequence attached to its 5' end.

More preferably, the amplification oligomers comprise an oligomer member that is SEQ ID NO:3. More preferably still, the amplification oligomers comprise an oligomer member that is SEQ ID NO:2 and an oligomer member that is SEQ ID NO:27, which further comprises a promoter sequence attached to its 5' end. More preferably, the amplification oligomers comprise an oligomer member that is SEQ ID NO:2 and an oligomer member that is SEQ ID NO:27 joined at its 5' end to SEQ ID NO:25. Most preferably, the amplification oligomers comprise first and second oligomer members that are SEQ ID NO:2 and SEQ ID NO:3. In another particularly preferred embodiment of amplification oligomers the amplification oligomers are configured to generate an amplicon comprising a target specific sequence that is from about 150 nucleotides in length to about 235 nucleotides in length, that is at least 80% identical to SEQ ID NO:43, and at least one amplification oligomer member of the amplification oligomers further comprises a promoter sequence. More preferably, the amplification oligomers are configured to generate an amplicon that comprises a target specific sequence that is from about 169 nucleotides in length to about 209 nucleotides in length and that is at least 90% identical to SEQ ID NO:43, and at least one amplification oligomer member of the amplification oligomers further comprises a promoter sequence. More preferably still, the amplification oligomers are configured to generate an amplicon that comprises a target specific sequence that is from about 178 nucleotides in length to about 198 nucleotides in length and that is at least 95% identical to SEQ ID NO:43, and at least one amplification oligomer member of the amplification oligomers further comprises a promoter sequence. And still more preferably, the amplification oligomers are configured to generate an amplicon that comprises a target specific sequence that is SEQ ID NO:43, and at least one amplification oligomer member of the amplification oligomers further comprises a promoter sequence. In one aspect of this alternate embodiment, the promoter sequences are preferably RNA polymerase promoter sequences, more preferably are T7 RNA Polymerase promoter sequences, and most preferably are SEQ ID NO:25.

Another embodiment of compositions for the amplification and detection of *A. vaginae* target nucleic acids includes detection probe oligomers. A preferred embodiment of detection probe oligomers, comprises those that specifically hybridize to a 16S rRNA of *A. vaginae*, specifically hybridize to a gene encoding a 16S rRNA of *A. vaginae* or specifically hybridize to an amplicon from either. A more particularly preferred embodiment of detection probe oligomers for detecting a 16S rRNA of *A. vaginae*, detecting a gene encoding a 16S rRNA of *A. vaginae* or detecting an amplicon from either, comprises those that specifically hybridize to an amplicon comprising a target specific sequence that is from about 150 nucleotides in length to about 235 nucleotides in length and is at least 80% identical to SEQ ID NO:43. More preferably, those that specifically hybridize to an amplicon comprising a target specific sequence that is from about 169 nucleotides in length to about 209 nucleotides in length and is at least 90% identical to SEQ ID NO:43. More preferably still, those that specifically hybridize to an amplicon comprising a target specific sequence that is from about 178 nucleotides in length to about 198 nucleotides in length and is at least 95% identical to SEQ ID NO:43. And most preferably, those that specifically hybridize to an amplicon comprising a target specific sequence that is SEQ ID NO:43. An alternative particularly preferred embodiment of detection probe oligomers for detecting a 16S rRNA of *A. vaginae*, detecting a gene encoding a 16S rRNA of *A. vaginae* or detecting an amplicon from either, are detection probe oligomers configured to specifically hybridize to all or a portion of a target sequence of a nucleic acid or amplified nucleic acid of 16S rRNA of *A. vaginae* or a gene encoding a 16S rRNA of *A. vaginae*, said region corresponding to from nucleotide 538 to nucleotide 566 of GenBank Accession No.: AF325325.1, gi:12240234 (SEQ ID NO:44). More preferably, the detection probe oligomers are configured to specifically hybridize to all or a portion of a region corresponding to from nucleotide 544 to nucleotide 566 of GenBank Accession No.: AF325325.1, gi:12240234 (SEQ ID NO:45). More preferably still, the detection probe oligomers are configured to specifically hybridize to all or a portion of a region corresponding to from nucleotide 548 to nucleotide 566 of GenBank Accession No.: AF325325.1, gi:12240234 (SEQ ID NO:46). More preferably still, the detection probe oligomers are configured to specifically hybridize to all or a portion of a region corresponding to from nucleotide 538 to nucleotide 558 of GenBank Accession No.: AF325325.1, gi:12240234 (SEQ ID NO:47). Most preferably, the detection probe oligomers are configured to specifically hybridize to a region corresponding to from nucleotide 548 to nucleotide 558 of GenBank Accession No.: AF325325.1, gi:12240234 (SEQ ID NO:48).

In another aspect of these preferred embodiments of detection probe oligomers there are detection probe oligomers from 11 nucleotides in length to 29 nucleotides in length, containing at least 11 nucleotides of SEQ ID NO:44, and that specifically hybridize with a sequence of a nucleic acid or an amplified nucleic acid of an *A. vaginae*. It is understood by ordinarily skilled artisans that an oligomer containing all or a part of a specified sequence (e.g., SEQ ID NO:44), may be configured to contain the complementary sequence, and/or the corresponding RNA or DNA sequence. Use of a reference sequence (e.g., SEQ ID NO:44) is for convenience. More preferred in this aspect, the detection probe oligomers are from 11 nucleotides in length to 29 nucleotides in length and contain a sequence corresponding SEQ ID NO:48. More preferred in this aspect, the detection probe oligomers are from 11 nucleotides in length to 29 nucleotides in length, contain a sequence corresponding to SEQ ID NO:48, and that specifically hybridize to all or a portion of a region of nucleic acid sequence or amplified nucleic acid sequence of an *A. vaginae* said region corresponding to from about nucleotide 538 to about nucleotide 566 of GenBank Accession No.: AF325325.1, gi:12240234 (SEQ ID NO:44). More preferred in this aspect, the detection oligomers are one of SEQ ID NOS:4, 15, 16 and 17. Most preferred in this aspect, the detection probe oligomer is SEQ ID NO:4.

In a further embodiment of the current invention there are provided kits, wherein said kits comprise at least one amplification oligomer or detection probe oligomer of the current invention. More preferably, said kits comprise at least an amplification oligomer combination of the current invention. More preferably, said kits comprise an amplification oligomer combination and a detection probe oligomer of the current invention. More preferably, said kits further comprise a target capture oligomer of the current invention. In one particular aspect, said kits comprise one or more of SEQ ID NOS:2, 3 & 4. In another particular aspect, said kits comprise one of more of SEQ ID NOS:2, 27 & 4.

One embodiment for a method of amplifying and detecting an *A. vaginae* target nucleic acid sequences includes in vitro assays. A preferred embodiment for amplifying in vitro a sequence of *A. vaginae* 16S rRNA or amplifying in vitro a sequence of a gene encoding *A. vaginae* 16S rRNA comprises the steps of contacting a sample with an amplification oligomer combination, wherein said amplification oligomer combination comprises a primer member selected from SEQ ID NOS:2, 9, 11, 12, 19, 27, 28, 29, 30, 31, 32, 36 & 38. More preferably, the two oligomers of the amplification oligomer combination are both primer members and are selected from SEQ ID NOS:2, 9, 11, 12, 19, 27, 28, 29, 30, 31, 32, 36 & 38. Particularly preferred primer members are SEQ ID NO:2 and SEQ ID NO:27.

Another preferred embodiment for amplifying in vitro a sequence of *A. vaginae* 16S rRNA or amplifying in vitro a sequence of a gene encoding *A. vaginae* 16S rRNA comprises the steps of contacting a sample with an amplification oligomer combination, wherein said amplification oligomer combination comprises a primer member and a promoter primer member. Preferably the primer member is selected from SEQ ID NOS:2, 9, 11, 12, 19, 31 & 32 and the promoter primer member is selected from SEQ ID NOS:3, 10, 13, 20, 35 & 37. More preferably the primer member is SEQ ID NO:2 and the promoter primer member is SEQ ID NO:27 joined at its 5' end to a promoter sequence, more preferably, the promoter primer member is SEQ ID NO:27 joined at its 5'end to an RNA Polymerase promoter sequence, more preferably joined at its 5'end to a T7 RNA polymerase promoter sequence, more preferably joined at its 5' end to SEQ ID NO:25, and most preferably the promoter primer member is SEQ ID NO:3.

Another particularly preferred amplification oligomer combination is configured to generate an amplicon comprising a target specific sequence that is from about 150 nucleotides in length to about 235 nucleotides in length and at least 80% identical to SEQ ID NO:43. More preferably the amplification oligomer combination is configured to specifically hybridize with a target sequence of an *A. vaginae* nucleic acid sequence to generate an amplicon comprising a target specific sequence that is from about 169 nucleotides in length to about 209 nucleotides in length and is at least 90% identical to SEQ ID NO:43. More preferably the amplification oligomer combination is configured to specifically hybridize with a target sequence of an *A. vaginae* nucleic acid sequence to generate an amplicon comprising a target specific sequence that is from about 178 nucleotides in length to about 198 nucleotides in length and is at least 95% identical to SEQ ID NO:43. Most preferably the amplification oligomer combination is configured to specifically hybridize with a target sequence of an *A. vaginae* nucleic acid sequence to generate an amplicon comprising a target specific sequence that is SEQ ID NO:43. In a preferred aspect of this instant embodiment, amplification oligomer combinations are configured to generate such amplicons, and said amplicons further comprise a promoter sequence.

In a further preferred aspect of an in vitro amplification and detection assay there is provided the step of providing a detection probe oligomer. Preferred detection probe oligomers specifically hybridize to all or a portion of a region of an *A. vaginae* nucleic acid sequence or amplified nucleic acid sequence that corresponds to from nucleotide 538 to nucleotide 566 of GenBank Accession No.: AF325325.1, gi:12240234 (SEQ ID NO:44). More preferably, detection probe oligomers specifically hybridize to all or a portion of a region of an *A. vaginae* nucleic acid or amplified nucleic acid sequence corresponding to from nucleotide 538 to nucleotide 566 of GenBank Accession No.: AF325325.1, gi:12240234 (SEQ ID NO:44), and said detection probe oligomers are from 11 nucleotides in length to 29 nucleotides in length. More preferably, detection probe oligomers contain a sequence corresponding to from nucleotide 548 to nucleotide 558 of GenBank Accession No.: AF325325.1, gi:12240234 (SEQ ID NO:48), and specifically hybridize to all or a portion of a region of an *A. vaginae* nucleic acid or amplified nucleic acid sequence corresponding to from about nucleotide 538 to about nucleotide 566 of GenBank Accession No.: AF325325.1, gi:12240234 (SEQ ID NO:44). More preferably, detection probe oligomers are from 11 nucleotides in length to 29 nucleotides in length, contain a sequence corresponding to from nucleotide 548 to nucleotide 558 of GenBank Accession No.: AF325325.1, gi:12240234 (SEQ ID NO:48), and specifically hybridize to all or a portion of a region of an *A. vaginae* nucleic acid or amplified nucleic acid, wherein said region corresponds to GenBank Accession No.: AF325325.1, gi:12240234 from nucleotide 538 to nucleotide 566 (SEQ ID NO:44); from nucleotide 544 to nucleotide 566 (SEQ ID NO:45); from nucleotide 548 to nucleotide 566 (SEQ ID NO:46); from nucleotide 538 to nucleotide 558 (SEQ ID NO:47); or from nucleotide 548 to nucleotide 558 (SEQ ID NO:45). Particularly preferred detection oligomers are selected from SEQ ID NOS:4, 15, 16 & 17. A most preferred detection probe oligomer is SEQ ID NO:4.

Thus, in one particularly preferred in vitro assay for the amplification and detection of *A. vaginae* nucleic acid there is provided an amplification oligomer combination comprising SEQ ID NO:2 and SEQ ID NO:3 for amplification of an *A. vaginae* target sequence and a detection probe oligomer comprising SEQ ID NO:4 for detecting *A. vaginae* nucleic acid or amplified nucleic acid sequences.

In a further preferred aspect of in vitro assays for amplification and detection of *A. vaginae* nucleic acid, the sample is a specimen from a human. More preferably, the sample is a vaginal swab specimen. More preferably, the sample is a cervical brush specimen. More preferably still, the sample is a specimen from a human and the in vitro assay is configured to diagnose bacterial vaginosis. More preferably still, the in vitro assay for amplification and detection of *A. vaginae* is configured to identify elevated numbers of *A. vaginae* nucleic acids over a base-line amount of *A. vaginae* nucleic acids.

BRIEF DESCRIPTION OF THE FIGURES

FIG. 1 illustrates a reference sequence *Atopobium vaginae* 16S ribosomal RNA gene, partial sequence found at GenBank under accession number AF325325.1 and GI:12240234 (Jan. 16, 2001), sometimes referred to herein when describing oligomers and regions.

FIGS. 2A-C: FIG. 2A illustrates an amplification oligomer combination. The amplification oligomer combination of this figure is shown targeting the reference sequence of FIG. 1, SID #1 is SEQ ID NO:1. The SID #2 oligomer is SEQ ID NO:2, the SID #27 oligomer is SEQ ID NO:27 and is also the target binding sequence of SEQ ID NO:3. FIG. 2B illustrates one strand of an amplicon generated by using the amplification oligomer combination shown in FIG. 2A on the nucleic acid sequence of SEQ ID NO:1. This exemplary amplicon's target specific sequence is SEQ ID NO:43 (shown as SID #43). Nucleotide residue numbering shown in the figure is that for the reference sequence of FIG. 1 (not shown). FIG. 2C illustrates a plurality of exemplary detection oligomers useful for detection of an amplicon similar to that shown in FIG. 2B. SID #1 is SEQ ID NO:1. Nucleotide residue numbering shown in the figure is that for the reference sequence of FIG.1.

DETAILED DESCRIPTION

Disclosed are compositions, kits and methods for amplifying and detecting *A. vaginae* nucleic acid from a sample, specifically sequences of *A. vaginae* 16S rRNA or genes encoding 16S rRNA. Preferably, the samples are biological samples. The compositions, kits and methods provide oligonucleotide sequences that recognize target sequences of *A. vaginae* 16S rRNA or their complementary sequences, or genes encoding 16S rRNA or their complementary sequences. Such oligonucleotides may be used as amplification oligonucleotides, which may include primers, promoter primers, blocked oligonucleotides, and promoter provider oligonucleotides, whose functions have been described previously (e.g., U.S. Pat. Nos. 4,683,195; 4,683,202; 4,800,159; 5,399,491; 5,554,516; 5,824,518; and 7,374,885). Other oligonucleotides may be used as probes for detecting amplified sequences of *A. vaginae*.

The methods provide for the sensitive and specific detection of *A. vaginae* nucleic acids. The methods include performing a nucleic acid amplification of *A. vaginae* sequences and detecting the amplified product, for example by specifically hybridizing the amplified product with a nucleic acid probe that provides a signal to indicate the presence of *A. vaginae* in the sample. The amplification step includes contacting the sample with one or more amplification oligomers specific for a target sequence in 16S rRNA to produce an amplified product if *A. vaginae* nucleic acid is present in the sample. Amplification synthesizes additional copies of the target sequence or its complement by using at least one nucleic acid polymerase to extend the sequence from an amplification oligomer (a primer) using a template strand. One embodiment for detecting the amplified product uses a hybridizing step that includes contacting the amplified product with at least one probe specific for a sequence amplified by the selected amplification oligomers, e.g., a sequence contained in the target sequence flanked by a pair of selected primers.

The detection step may be performed using any of a variety of known ways to detect a signal specifically associated with the amplified target sequence, such as by hybridizing the amplification product with a labeled probe and detecting a signal resulting from the labeled probe. The detection step may also provide additional information on the amplified sequence, such as all or a portion of its nucleic acid base sequence. Detection may be performed after the amplification reaction is completed, or may be performed simultaneous with amplifying the target region, e.g., in real time. In one embodiment, the detection step allows homogeneous detection, e.g., detection of the hybridized probe without removal of unhybridized probe from the mixture (e.g., U.S. Pat. Nos. 5,639,604 and 5,283,174).

In embodiments that detect the amplified product near or at the end of the amplification step, a linear probe may be used to provide a signal to indicate hybridization of the probe to the amplified product. One example of such detection uses a luminescently labeled probe that hybridizes to target nucleic acid. Luminescent label is then hydrolyzed from non-hybridized probe. Detection is performed by chemiluminescence using a luminometer. (e.g., WO 89/002476). In other embodiments that use real-time detection, the probe may be a hairpin probe, such as a molecular beacon, molecular torch, or hybridization switch probe, that is labeled with a reporter moiety that is detected when the probe binds to amplified product. Such probes may comprise target binding sequences and non-target binding sequences. Various forms of such probes have been described previously (e.g., U.S. Pat. Nos. 5,118,801; 5,312,728; 5,925,517; 6,150,097; 6,849,412; 6,835,542; 6,534,274; and 6,361,945; and US Pub. Nos. 20060068417A1; and US Pub. No. 20060194240A1).

To aid in understanding aspects of the invention, some terms used herein are described in more detail. All other scientific and technical terms used herein have the same meaning as commonly understood by those skilled in the relevant art, such as may be provided in Dictionary of *Microbiology and Molecular Biology*, 2nd ed. (Singleton et al., 1994, John Wiley & Sons, New York, N.Y.), *The Harper Collins Dictionary of Biology* (Hale & Marham, 1991, Harper Perennial, New York, N.Y.), and other references cited herein. Unless mentioned otherwise, the techniques employed or contemplated herein are standard methods well known to a person of ordinary skill in the art of molecular biology.

It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein.

"Sample" includes any specimen that may contain *A. vaginae* or components thereof, such as nucleic acids or fragments of nucleic acids. Samples include "biological samples" which include any tissue or material derived from a living or dead human that may contain *A. vaginae* or target nucleic acid derived therefrom, including, e.g., vaginal swab samples, cervical brush samples, respiratory tissue or exudates such as bronchoscopy, bronchoalveolar lavage (BAL) or lung biopsy, sputum, saliva, peripheral blood, plasma, serum, lymph node, gastrointestinal tissue, feces, urine, semen or other body fluids or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see PCT Pub. No. WO 95/32305), phosphorothioate linkages, methylphosphonate linkages, or combinations thereof. Sugar moieties of the nucleic acid may be either ribose or deoxyribose, or similar compounds having known substitutions; e.g., 2' methoxy substitutions and 2' halide substitutions (e.g., 2'-F). Nitrogenous bases may be conventional bases (A, G, C, T, U), analogs thereof (e.g., inosine, 5-methylisocytosine, isoguanine; *The Biochemistry of the Nucleic Acids* 5-36, Adams et al., ed., 11th ed., 1992, Abraham et al., 2007, BioTechniques 43: 617-24), which include derivatives of purine or pyrimidine bases (e.g., $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, O.sup.6-methylguanine, 4-thio-pyrimidines, 4-amino-pyrimidines, 4-dimethylhydrazine-pyrimidines, and O.sup.4-alkyl-pyrimidines, and pyrazolo-compounds, such as unsubstituted or 3-substituted pyrazolo[3,4-d]pyrimidine; U.S. Pat. Nos. 5,378,825, 6,949, 367 and PCT Pub. No. WO 93/13121). Nucleic acids may include "abasic" residues in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., 2004, *Biochemistry* 43(42):13233-41). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

The term "polynucleotide" as used herein denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid.

A "nucleotide" as used herein is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

A "non-nucleotide unit" as used herein is a unit that does not significantly participate in hybridization of a polymer. Such units must not, for example, participate in any significant hydrogen bonding with a nucleotide, and would exclude units having as a component one of the five nucleotide bases or analogs thereof.

A "target nucleic acid" as used herein is a nucleic acid comprising a "target sequence" to be amplified. Target nucleic acids may be DNA or RNA as described herein, and may be either single-stranded or double-stranded. The target nucleic acid may include other sequences besides the target sequence, which may not be amplified. Typical target nucleic acids include virus genomes, bacterial genomes, fungal genomes, plant genomes, animal genomes, rRNA, tRNA, or mRNA from viruses, bacteria or eukaryotic cells, mitochondrial DNA, or chromosomal DNA.

By "isolated" it is meant that a sample containing a target nucleic acid is taken from its natural milieu, but the term does not connote any degree of purification.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during the processes of TMA. Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

"Target binding sequence" is used herein to refer to the portion of an oligomer that is configured to hybridize with a target nucleic acid sequence. Preferably, the target binding sequences are configured to specifically hybridize with a target nucleic acid sequence. Target binding sequences may be 100% complementary to the portion of the target sequence to which they are configured to hybridize; but not necessarily. Target-binding sequences may also include inserted, deleted and/or substituted nucleotide residues relative to a target sequence. Less than 100% complementarity of a target binding sequence to a target sequence may arise, for example, when the target nucleic acid is a plurality strains within a species, such as would be the case for an oligomer configured to hybridize to the various strains of *A. vaginae*. It is understood that other reasons exist for configuring a target binding sequence to have less than 100% complementarity to a target nucleic acid.

The term "targets a sequence" as used herein in reference to a region of *A. vaginae* nucleic acid refers to a process whereby an oligonucleotide hybridizes to the target sequence in a manner that allows for amplification and detection as described herein. In one preferred embodiment, the oligonucleotide is complementary with the targeted *A. vaginae* nucleic acid sequence and contains no mismatches. In another preferred embodiment, the oligonucleotide is complementary but contains 1; or 2; or 3; or 4; or 5 mismatches with the targeted *A. vaginae* nucleic acid sequence. Preferably, the oligonucleotide that hybridizes to the *A. vaginae* nucleic acid sequence includes at least 10 to as many as 50 nucleotides complementary to the target sequence. It is understood that at least 10 and as many as 50 is an inclusive range such that 10, 50 and each whole number there between are included. Preferably, the oligomer specifically hybridizes to the target sequence.

The term "configured to" denotes an actual arrangement of the polynucleotide sequence configuration of the references oligonucleotide target hybridizing sequence. For example, amplification oligomers that are configured to generate a specified amplicon from a target sequence have polynucleotide sequences that hybridize to the target sequence and can be used in an amplification reaction to generate the amplicon. Also as an example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target hybridizing region of an amplification oligonucleotide, detection probe or other oligonucleotide is designed to have a polynucleotide sequence that could target a sequence of the referenced *A. vaginae* target region. Such an oligonucleotide is not limited to targeting that sequence only, but is rather useful as a composition, in a kit or in a method for targeting a *A. vaginae* target nucleic acid. The oligonucleotide is designed to function as a component of an assay for amplification and detection of *A. vaginae* from a sample, and therefore is designed to target *A. vaginae* in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined. The term "configured to" denotes an actual arrangement of the polynucleotide sequence configuration of the amplification oligonucleotide target hybridizing sequence.

The term "fragment" as used herein in reference to the *A. vaginae* targeted nucleic acid sequence refers to a piece of contiguous nucleic acid. In certain embodiments, the fragment includes contiguous nucleotides from an *A. vaginae* 16S ribosomal RNA, wherein the number of 16S contiguous nucleotides in the fragment are less than that for the entire 16S.

The term "region" as used herein refers to a portion of a nucleic acid wherein said portion is smaller than the entire nucleic acid. For example, when the nucleic acid in reference is an oligonucleotide promoter primer, the term "region" may be used refer to the smaller promoter portion of the entire oligonucleotide. Similarly, and also as example only, when the nucleic acid is a 16S ribosomal RNA, the term "region" may be used to refer to a smaller area of the nucleic acid, wherein the smaller area is targeted by one or more oligonucleotides of the invention. As a non-limiting example, when the nucleic acid in reference is an amplicon, the term region, the term region may be used to refer to the smaller nucleotide sequence identified for hybridization by the target binding sequence of a probe.

The interchangeable terms "oligomer," "oligo" and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources, but or may be synthesized using any of a variety of well known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase, it may function as a primer and provide a promoter if it contains a sequence recognized by an RNA polymerase and allows for transcription (e.g., a T7 Primer), and it may function to detect a target nucleic acid if it is capable of hybridizing to the target nucleic acid, or amplicon thereof, and further provides a detectible moiety (e.g., an acridinium-ester compound).

As used herein, an oligonucleotide having a nucleic acid sequence "comprising" or "consisting of" or "consisting essentially of" a sequence selected from a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

"Consisting essentially of" is used to mean that additional component(s), composition(s) or method step(s) that do not materially change the basic and novel characteristics of the present invention may be included in the compositions or kits or methods of the present invention. Such characteristics include the ability to detect *A. vaginae* nucleic acid in a biological sample. Other characteristics include limited cross-reactivity with other Bacteria or mammalian nucleic acid and targeting 16S rRNA. Any component(s), composition(s), or method step(s) that have a material effect on the basic and novel characteristics of the present invention would fall outside of this term.

As used herein, an oligonucleotide "substantially corresponding to" a specified nucleic acid sequence means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from the referred to sequence and still hybridize to the same target nucleic acid sequence. It is also understood that a first nucleic acid corresponding to a second nucleic acid includes the complements thereof and includes the RNA and DNA thereof. This variation from the nucleic acid may be stated in terms of a percentage of identical bases within the sequence or the percentage of perfectly complementary bases between the probe or primer and its target sequence. Thus, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage can be from 100% to about 90%; in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

A "helper oligonucleotide" or "helper" refers to an oligonucleotide designed to bind to a target nucleic acid and impose a different secondary and/or tertiary structure on the target to increase the rate and extent of hybridization of a detection probe or other oligonucleotide with the targeted nucleic acid, as described, for example, in U.S. Pat. No. 5,030,557. Helpers may also be used to assist with the hybridization to target nucleic acid sequences and function of primer, target capture and other oligonucleotides.

As used herein, a "blocking moiety" is a substance used to "block" the 3'-terminus of an oligonucleotide or other nucleic acid so that it cannot be efficiently extended by a nucleic acid polymerase. Oligomers not intended for extension by a nucleic acid polymerase may include a blocker group that replaces the 3'OH to prevent enzyme-mediated extension of the oligomer in an amplification reaction. For example, blocked amplification oligomers and/or detection probes present during amplification may not have functional 3'OH and instead include one or more blocking groups located at or near the 3' end. In some embodiments a blocking group near the 3' end may be within five residues of the 3' end and is sufficiently large to limit binding of a polymerase to the oligomer. In other embodiments a blocking group is covalently attached to the 3' terminus. Many different chemical groups may be used to block the 3' end, e.g., alkyl groups, non-nucleotide linkers, alkane-diol dideoxynucleotide residues, and cordycepin.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter-primer" or "promoter provider"). Those skilled in the art will understand that an amplification oligomer that functions as a primer may be modified to include a 5' promoter sequence, and thus function as a promoter-primer. Incorporating a 3' blocked end further modifies the promoter-primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon or other nucleic acid, that the range is inclusive of all whole numbers (e.g. 19-25 contiguous nucleotides in length includes 19, 20, 21, 22, 23, 24 & 25).

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter-provider" or "provider" refers to an oligonucleotide comprising first and second regions, and which is modified to prevent the initiation of DNA synthesis from its 3'-terminus. The "first region" of a promoter-provider oligonucleotide comprises a base sequence which hybridizes to a DNA template, where the hybridizing sequence is situated 3', but not necessarily adjacent to, a promoter region. The hybridizing portion of a promoter oligonucleotide is typically at least 10 nucleotides in length, and may extend up to 50 or more nucleotides in length. The "second region" comprises a promoter sequence for an RNA polymerase. A promoter oligonucleotide is engineered so that it is incapable of being extended by an RNA- or DNA-dependent DNA polymerase, e.g., reverse transcriptase, preferably comprising a blocking moiety at its 3'-terminus as described above. As referred to herein, a "T7

Provider" is a blocked promoter-provider oligonucleotide that provides an oligonucleotide sequence that is recognized by T7 RNA polymerase.

As used herein, a "terminating oligonucleotide" or "blocker oligonucleotide" is an oligonucleotide comprising a base sequence that is complementary to a region of the target nucleic acid in the vicinity of the 5'-end of the target sequence, so as to "terminate" primer extension of a nascent nucleic acid that includes a priming oligonucleotide, thereby providing a defined 3'-end for the nascent nucleic acid strand.

An "extender oligomer" or "extend oligomer" as used herein refers to an oligonucleotide that is the same sense as the T7 Provider and may act as a helper oligonucleotide that opens up structure or improves specificity.

"Amplification" refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), ligase chain reaction (LCR), strand-displacement amplification (SDA), and transcription-mediated or transcription-associated amplification. Replicase-mediated amplification uses self-replicating RNA molecules, and a replicase such as QB-replicase (e.g., U.S. Pat. No. 4,786,600). PCR amplification uses a DNA polymerase, pairs of primers, and thermal cycling to synthesize multiple copies of two complementary strands of dsDNA or from a cDNA (e.g., U.S. Pat. Nos. 4,683,195, 4,683,202, and 4,800,159). LCR amplification uses four or more different oligonucleotides to amplify a target and its complementary strand by using multiple cycles of hybridization, ligation, and denaturation (e.g., U.S. Pat. Nos. 5,427,930 and 5,516, 663). SDA uses a primer that contains a recognition site for a restriction endonuclease and an endonuclease that nicks one strand of a hemimodified DNA duplex that includes the target sequence, whereby amplification occurs in a series of primer extension and strand displacement steps (e.g., U.S. Pat. Nos. 5,422,252; 5,547,861; and 5,648,211).

"Transcription associated amplification" or "transcription mediated amplification" (TMA) refer to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods and single-primer transcription associated amplification method are embodiments of amplification methods used for detection of *A. vaginae* target sequences as described herein. Variations of transcription-associated amplification are well known in the art as previously disclosed in detail (e.g., U.S. Pat. Nos. 4,868,105; 5,124,246; 5,130,238; 5,399,491; 5,437,990; 5,554,516; and 7,374,885; and PCT Pub. Nos. WO 88/01302; WO 88/10315 and WO 95/03430). The person of ordinary skill in the art will appreciate that the disclosed compositions may be used in amplification methods based on extension of oligomer sequences by a polymerase.

As used herein, the term "real-time TMA" refers to single-primer transcription-mediated amplification ("TMA") of target nucleic acid that is monitored by real-time detection means.

The term "amplicon" or the term "amplification product" as used herein refers to the nucleic acid molecule generated during an amplification procedure that is complementary or homologous to a sequence contained within the target sequence. The complementary or homologous sequence of an amplicon is sometimes referred to herein as a "target-specific sequence." Amplicons generated using the amplification oligomers of the current invention may comprise non-target specific sequences. Amplicons can be double stranded or single stranded and can include DNA, RNA or both. For example, DNA-dependent RNA polymerase transcribes single stranded amplicons from double stranded DNA during transcription-mediated amplification procedures. These single stranded amplicons are RNA amplicons and can be either strand of a double stranded complex; depending on how the amplification oligomers are configured. Thus, amplicons can be single stranded RNA. RNA-dependent DNA polymerases synthesize a DNA strand that is complementary to an RNA template. Thus, amplicons can be double stranded DNA and RNA hybrids. RNA-dependent DNA polymerases often include RNase activity, or are used in conjunction with an RNase, which degrades the RNA strand. Thus, amplicons can be single stranded DNA. RNA-dependent DNA polymerases and DNA-dependent DNA polymerases synthesize complementary DNA strands from DNA templates. Thus, amplicons can be double stranded DNA. RNA-dependent RNA polymerases synthesize RNA from an RNA template. Thus, amplicons can be double stranded RNA. DNA Dependent RNA polymerases synthesize RNA from double stranded DNA templates, also referred to as transcription. Thus, amplicons can be single stranded RNA. Amplicons and methods for generating amplicons are known to those skilled in the art. For convenience herein, a single strand of RNA or a single strand of DNA may represent an amplicon generated by an amplification oligomer combination of the current invention. Such representation is not meant to limit the amplicon to the representation shown. Skilled artisans in possession of the instant disclosure will use amplification oligomers and polymerase enzymes to generate any of the numerous types of amplicons; all within the spirit of the current invention.

A "non-target-specific sequence," as is used herein refers to a region of an oligomer sequence, wherein said region does not stably hybridize with a target sequence under standard hybridization conditions. Oligomers with non-target-specific sequences include, but are not limited to, promoter primers, and molecular beacons. An amplification oligomer may contain a sequence that is not complementary to the target or template sequence; for example, the 5' region of a primer may include a promoter sequence that is non-complementary to the target nucleic acid (referred to as a "promoter-primer"). Those skilled in the art will understand that an amplification oligomer that functions as a primer may be modified to include a 5' promoter sequence, and thus function as a promoter-primer. Similarly, a promoter-primer may be modified by removal of, or synthesis without, a promoter sequence and still function as a primer. A 3' blocked amplification oligomer may provide a promoter sequence and serve as a template for polymerization (referred to as a "promoter provider"). Thus, an amplicon that is generated by an amplification oligomer member such as a promoter primer will comprise a target-specific sequence and a non-target-specific sequence.

"Probe," "detection probe" or "detection oligonucleotide" are terms referring to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Probes may be DNA, RNA, analogs thereof or combinations thereof and they may be labeled or unlabeled. A probe's "target sequence" generally refers to a smaller nucleic acid sequence region within a larger nucleic acid sequence that hybridizes specifically to at least a portion of a probe oligomer by standard base pairing. A probe may comprise target-specific sequences and other sequences that contribute to the three-dimensional conformation of the probe (e.g., U.S. Pat. Nos. 5,118,801; 5,312,728; 6,849,412; 6,835,542; 6,534,274; and 6,361,945; and US Pub. No. 20060068417).

By "stable" or "stable for detection" is meant that the temperature of a reaction mixture is at least 2° C. below the melting temperature of a nucleic acid duplex.

As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g. hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (e.g., U.S. Pat. Nos. 5,283,174, 5,656,207, and 5,658,737). Labels include chemiluminescent compounds, e.g., acridinium ester ("AE") compounds that include standard AE and derivatives (e.g., U.S. Pat. Nos. 5,656,207, 5,658,737, and 5,639,604). Synthesis and methods of attaching labels to nucleic acids and detecting labels are well known (e.g., Sambrook et al., *Molecular Cloning, A Laboratory Manual,* 2nd ed. (Cold Spring Harbor Laboratory Press, Cold Spring Harbor, N.Y., 1989), Chapter 10; U.S. Pat. Nos. 5,658,737, 5,656,207, 5,547,842, 5,283,174, and 4,581,333). More than one label, and more than one type of label, may be present on a particular probe, or detection may use a mixture of probes in which each probe is labeled with a compound that produces a detectable signal (e.g., U.S. Pat. Nos. 6,180,340 and 6,350,579).

As used herein, a "capture oligonucleotide" or "capture probe" refers to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a sequence-binding region (e.g., target-specific portion) and an immobilized probe-binding region, usually on the same oligomer, although the two regions may be present on two different oligomers joined together by one or more linkers. Another embodiment of a capture oligomer uses a target-sequence binding region that includes random or non-random poly-GU, poly-GT, or poly U sequences to bind non-specifically to a target nucleic acid and link it to an immobilized probe on a support.

As used herein, an "immobilized oligonucleotide", "immobilized probe" or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size ±5%), to which an immobilized probe is joined directly (via covalent linkage, chelation, or ionic interaction), or indirectly (via one or more linkers), where the linkage or interaction between the probe and support is stable during hybridization conditions.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g. G:C, A:T or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues, including abasic residues, that are not complementary. Sufficiently complementary contiguous sequences typically are at least 80%, or at least 90%, complementary to a sequence to which an oligomer is intended to specifically hybridize. Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "completely" complementary, (e.g., Sambrook et al., *Molecular Cloning, A Laboratory Manual,* $2^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57). It is understood that ranges for percent identity are inclusive of all whole and partial numbers (e.g., at least 90% includes 90, 91, 93.5, 97.687 and etc.).

By "preferentially hybridize" or "specifically hybridize" is meant that under stringent hybridization assay conditions, probes hybridize to their target sequences, or replicates thereof, to form stable probe: target hybrids, while at the same time formation of stable probe: non-target hybrids is minimized Thus, a probe hybridizes to a target sequence or replicate thereof to a sufficiently greater extent than to a non-target sequence, to enable one having ordinary skill in the art to accurately quantitate the RNA replicates or complementary DNA (cDNA) of the target sequence formed during the amplification. Appropriate hybridization conditions are well known in the art, may be predicted based on sequence composition, or can be determined by using routine testing methods (e.g., Sambrook et al., *Molecular Cloning, A Laboratory Manual*, 2$^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57).

By "nucleic acid hybrid" or "hybrid" or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

"Sample preparation" refers to any steps or method that treats a sample for subsequent amplification and/or detection of *A. vaginae* nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and PCT Pub. No. WO 2008/016988).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, or at least 80%, or at least 95% of the target nucleic acid from other sample components.

As used herein, a "DNA-dependent DNA polymerase" is an enzyme that synthesizes a complementary DNA copy from a DNA template. Examples are DNA polymerase I from *E. coli*, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

As used herein, a "DNA-dependent RNA polymerase" or "transcriptase" is an enzyme that synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from *E. coli* and bacteriophages T7, T3, and SP6.

As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required to initiate synthesis with both RNA and DNA templates.

As used herein, a "selective RNAse" is an enzyme that degrades the RNA portion of an RNA:DNA duplex but not single-stranded RNA, double-stranded RNA or DNA. An exemplary selective RNAse is RNAse H. Enzymes possessing the same or similar activity as RNAse H may also be used. Selective RNAses may be endonucleases or exonucleases. Most reverse transcriptase enzymes contain an RNAse H activity in addition to their polymerase activities. However, other sources of the RNAse H are available without an associated polymerase activity. The degradation may result in separation of RNA from a RNA:DNA complex. Alternatively, a selective RNAse may simply cut the RNA at various locations such that portions of the RNA melt off or permit enzymes to unwind portions of the RNA. Other enzymes that selectively degrade RNA target sequences or RNA products of the present invention will be readily apparent to those of ordinary skill in the art.

The term "specificity," in the context of an amplification and/or detection system, is used herein to refer to the characteristic of the system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

As used herein, a "colony-forming unit" ("CFU") is used as a measure of viable microorganisms in a sample. A CFU is an individual viable cell capable of forming on a solid medium a visible colony whose individual cells are derived by cell division from one parental cell. One CFU corresponds to ~1000 copies of rRNA.

As used herein, the term "relative light unit" ("RLU") is an arbitrary unit of measurement indicating the relative number of photons emitted by the sample at a given wavelength or band of wavelengths. RLU varies with the characteristics of the detection means used for the measurement.

The invention includes methods of amplifying and detecting *A. vaginae* nucleic acid, specifically sequences of the 16S rRNA of *A. vaginae* or genes encoding the 16S rRNA of *A. vaginae*. The invention includes oligonucleotide sequences that specifically recognize target sequences of the 16S rRNA of *A. vaginae* or their complementary sequences, or genes encoding the 16S rRNA of *A. vaginae* or their complementary sequences. Such oligonucleotide sequences may be used as amplification oligomers, which may include primers, promoter primers, blocked oligomers, and promoter provider oligomers, whose functions have been generally described previously (e.g., U.S. Pat. Nos. 5,399,491, 5,554, 516 and 5,824,518, Kacian et al.; U.S. Pat. No. 7,374,885 A1, Becker et al.; and U.S. Pat. Nos. 4,683,195, 4,683,202, and 4,800,159, Mullis et al.). Other embodiments of the oligonucleotide sequences may be used as probes for detecting amplified sequences of 16S rRNA from *A. vaginae*.

Transcription Mediated Amplification.

Amplification methods that use TMA amplification include the following steps. Briefly, the target nucleic acid that contains the sequence to be amplified is provided as single stranded nucleic acid (e.g., ssRNA or ssDNA). Those skilled in the art will appreciate that conventional melting of double stranded nucleic acid (e.g., dsDNA) may be used to provide single-stranded target nucleic acids. A promoter primer binds specifically to the target nucleic acid at its target sequence and a reverse transcriptase (RT) extends the 3' end of the promoter primer using the target strand as a template to create a cDNA copy of the target sequence strand, resulting in an RNA:DNA duplex. An RNase digests the RNA strand of the RNA:DNA duplex and a second primer binds specifically to its target sequence, which is located on the cDNA strand downstream from the promoter-primer end. RT synthesizes a new DNA strand by extending the 3' end of the second primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the second primer binds specifically to its target sequence in each of the amplicons and RT creates a DNA copy from the amplicon RNA template to produce an RNA:DNA duplex. RNase in the reaction mixture digests the amplicon RNA from the RNA:DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

Detection of the amplified products may be accomplished by a variety of methods. The nucleic acids may be associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid probes that are complementary to a sequence in the amplified product and detecting the presence of the probe:product complex, or by using a complex of probes that may amplify the detectable signal associated with the amplified products (e.g., U.S. Pat. Nos. 5,424,413 and 5,451,503, Hogan et al., U.S. Pat. No. 5,849,481, Urdea et al.). Directly or indirectly labeled probes that specifically associate with the amplified product provide a detectable signal that indicates the presence of the target nucleic acid in the sample. For example, if the target nucleic acid is the 16S rRNA of *A. vaginae*, the amplified product will contain a target sequence in or complementary to a sequence in the 16S rRNA of *A. vaginae*, and a probe will bind directly or indirectly to a sequence contained in the amplified product to indicate the presence of the 16S rRNA of *A. vaginae* in the tested sample.

Preferred embodiments of probes that hybridize to the complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified *A. vaginae* rRNA sequences may be unlabeled and detected indirectly (e.g., by binding of another binding partner to a moiety on the probe) or may be labeled with a variety of detectable labels. Preferred embodiments of labels include compounds that emit a detectable light signal, e.g., fluorophores or luminescent compounds that can be detected in a homogeneous mixture. More than one label, and more than one type of label, may be present on a particular probe, or detection may rely on using a mixture of probes in which each probe is labeled with a compound that produces a detectable signal (e.g., U.S. Pat. Nos. 6,180,340 and 6,350,579, Nelson). Labels may be attached to a probe by various means including covalent linkages, chelation, and ionic interactions, but preferably the label is covalently attached. Probes may be linear oligomers that do not substantially form conformations held by intramolecular bonds or oligomers that form conformations generally referred to as hairpins by using intramolecular hybridization. Preferred embodiments of linear oligomers generally include a chemiluminescent compound as the label, preferably an AE compound.

Preferred embodiments of a hairpin probes include the "molecular torch" (e.g., U.S. Pat. Nos. 6,849,412, 6,835, 542, 6,534,274, and 6,361,945, Becker et al., the details of which are incorporated by reference herein) and the "molecular beacon." (Tyagi et al., 1998, Nature Biotechnol. 16:49-53, U.S. Pat. Nos. 5,118,801 and 5,312,728, Lizardi et al., the details of which are incorporated by reference herein). Methods for using such hairpin probes are well known in the art.

Oligomers that are not intended to be extended by a nucleic acid polymerase preferably include a blocker group that replaces the 3' OH to prevent enzyme-mediated extension of the oligomer in an amplification reaction. For example, blocked amplification oligomers and/or detection probes present during amplification preferably do not have a functional 3' OH and instead include one or more blocking groups located at or near the 3' end. A blocking group near the 3' end is preferably within five residues of the 3' end and is sufficiently large to limit binding of a polymerase to the oligomer, and other preferred embodiments contain a blocking group covalently attached to the 3' terminus. Many different chemical groups may be used to block the 3' end, e.g., alkyl groups, non-nucleotide linkers, alkane-diol dideoxynucleotide residues, and cordycepin. A preferred method for detecting *A. vaginae* 16S rRNA sequences uses a transcription-associated amplification with a linear chemiluminescently labeled probe, more preferably, a linear AE labeled probe.

Preparation of samples for amplification and detection of *A. vaginae* 16S rRNA sequences may include methods of separating and/or concentrating organisms contained in a sample from other sample components. Sample preparation may also include routine methods of disrupting cells or lysing bacteria to release intracellular contents, including the 16S rRNA of *A. vaginae* or genetic sequences encoding the 16S rRNA of *A. vaginae*. Sample preparation before amplification may further include an optional step of target capture to specifically or non-specifically separate the target nucleic acids from other sample components. Nonspecific target capture methods may involve selective precipitation of nucleic acids from a substantially aqueous mixture, adherence of nucleic acids to a support that is washed to remove other sample components, or other means of physically separating nucleic acids from a mixture that contains *A. vaginae* nucleic acid and other sample components.

In a preferred embodiment, the 16S rRNA of *A. vaginae* or genes encoding the 16S rRNA of *A. vaginae* are selectively separated from other sample components by specifically hybridizing the *A. vaginae* nucleic acid to a capture oligomer specific for the *A. vaginae* 16S rRNA target sequence to form a target sequence:capture probe complex that is separated from sample components. A preferred method of specific target capture binds the *A. vaginae* 16S rRNA target:capture probe complex to an immobilized probe to form a target:capture probe:immobilized probe complex that is separated from the sample and, optionally, washed to remove non-target sample components, as previously described (U.S. Pat. Nos. 6,110,678, 6,280,952, and 6,534,273, Weisburg et al., the details of which are incorporated by reference herein). Briefly, the capture probe oligomer includes a target sequence that specifically binds to the *A. vaginae* 16S rRNA target sequence in the 16S rRNA of *A. vaginae* or in a gene encoding the 16S rRNA of *A. vaginae* and also includes a specific binding partner that attaches the capture probe with its bound target sequence to a solid support, to facilitate separating the target sequence from the sample components. In a preferred embodiment, the specific binding partner of the capture probe is a 3' "tail" sequence that is not complementary to the *A. vaginae* 16S rRNA target sequence but that hybridizes to a complementary sequence on an immobilized probe attached to a solid support. Any sequence may be used in a tail region, which is generally about 5 to 50 nt long, and preferred embodiments include a substantially homopolymeric tail of about 10 to 40 nt (e.g., $A_{10}$ to $A_{40}$), more preferably about 14 to 33 nt (e.g., $A_{14}$ to $A_{30}$ or $T_3A_{14}$ to $T_3A_{30}$), that bind to a complementary immobilized sequence (e.g., poly-T) attached to a solid support, e.g., a matrix or particle. Target capture preferably occurs in a solution phase mixture that contains one or more capture oligomers that hybridize specifically to the 16S rRNA of *A. vaginae* or gene target sequence under hybridizing conditions, usually at a temperature higher than the Tm of the tail sequence:immobilized probe sequence duplex. Then, the *A. vaginae* 16S rRNA target:capture probe complex is captured by adjusting the hybridization conditions so that the capture probe tail hybridizes to the immobilized probe, and the entire complex on the solid support is then separated from other sample components. The support with the attached immobilized probe:capture probe: *A. vaginae* 16S rRNA target sequence may be washed one or more times to further remove other sample components. Preferred embodiments use a particulate solid support, such as paramagnetic beads, so that particles with the attached *A. vaginae* 16S rRNA target:capture probe:immobilized probe complex may be suspended in a washing solution and retrieved from the washing solution, preferably by using magnetic attraction. To limit the number of handling steps, the *A. vaginae* 16S rRNA target nucleic acid may be amplified by simply mixing the *A. vaginae* 16S rRNA target sequence in the complex on the support with amplification oligomers and proceeding with amplification steps.

Assays for detection of the *A. vaginae* 16S rRNA nucleic acid may optionally include a non-*A. vaginae* 16S rRNA internal control (IC) nucleic acid that is amplified and detected in the same assay reaction mixtures by using amplification and detection oligomers specific for the IC sequence. IC nucleic acid sequences can be synthetic nucleic acid sequences that are spiked into a sample or the IC nucleic acid sequences may be cellular component. IC nucleic acid sequences that are cellular components can be from exogenous cellular sources or endogenous cellular sources relative to the specimen. An exogenous cellular source, for example, is a cell that is added into the sample and that then flows through the sample processing procedures along with the specimen. A more particular example would be the addition of a HeLa cell, Jurkat cell, SiLa cell or other to the sample medium along with the specimen that is collected for testing (e.g., a vaginal swab specimen). The specimen and the exogenous cells are then processed, amplified and detected. The specimen being amplified and detected using amplification and detection oligomers for identifying the target sequence of interest and the exogenous cells being amplified and detected using amplification and detection oligomers for identifying an IC target sequence such as 18S rRNA. An endogenous cellular source is a cellular source that would naturally be obtained when gathering the specimen. One example; epithelial cells will present when obtaining a specimen via a vaginal swab. Similar then to the above exemplary exogenous cells process described, the specimen and the endogenous cellular source are both processed, amplified and detected. The specimen being amplified and detected using amplification and detection oligomers for identifying the target sequence of interest and the endogenous cells being amplified and detected using amplification and detection oligomers for identifying an IC target sequence; typically a housekeeping gene present in the endogenous cellular source, such as a beta-globulin gene. (See e.g., Poljak et al., J. Clin. Virol (2002), 25: S89-97; U.S. Pat. No. 6,410,321; and U.S. Pub. No. 2004-0023288). Use of a cellular source IC allows for a control from sample collection through detection. Synthetic nucleic acid sequences provide for control of amplification and detection.

In one aspect, amplification and detection of a signal from the amplified IC sequence demonstrates that the assay reagents, conditions, and performance of assay steps were properly used in the assay if no signal is obtained for the intended target *A. vaginae* nucleic acid (e.g., samples that test negative for the 16S rRNA of *A. vaginae*). An IC may also be used as an internal calibrator for the assay when a quantitative result is desired, i.e., the signal obtained from the IC amplification and detection is used to set a parameter used in an algorithm for quantitating the amount of *A. vaginae* nucleic acid in a sample based on the signal obtained for amplified an *A. vaginae* 16S rRNA target sequence. ICs are also useful for monitoring the integrity of one or more steps in an assay. A preferred embodiment of a synthetic IC nucleic acid sequence is a randomized sequence that has been derived from a naturally occurring source (e.g., an HIV sequence that has been rearranged in a random manner). Another preferred IC nucleic acid sequence may be an RNA transcript isolated from a naturally occurring source or synthesized in vitro, such as by making transcripts from a cloned randomized sequence such that the number of copies of IC included in an assay may be accurately determined. The primers and probe for the IC target sequence are configured and synthesized by using any well known method provided that the primers and probe function for amplification of the IC target sequence and detection of the amplified IC sequence using substantially the same assay conditions used to amplify and detect the *A. vaginae* target sequence. In preferred embodiments that include a target capture-based purification step, it is preferred that a target capture probe specific for the IC target be included in the assay in the target capture step so that the IC is treated in the assay in a manner analogous to that for the intended *A. vaginae* analyte in all of the assay steps.

Assays for detection of the *A. vaginae* 16S rRNA nucleic acid may optionally include a pseudotarget. A "pseudotarget" is an oligonucleotide that can be co-amplified with the target polynucleotide in a single amplification reaction. The pseudotarget and target polynucleotide may be amplified using the same set of oligonucleotide primers. The pseudotarget and the target polynucleotide will be non-identical molecules so that the target probe will not detect the pseudotarget.

Amplification methods using pseudotargets are useful for quantifying target polynucleotides present in a test sample. These methods includes steps for: (1) obtaining a test sample that contains an unknown amount of an target polynucleotide; (2) combining a predetermined amount of this test sample with a predetermined amount of a pseudotarget; (3) co-amplifying in an amplification reaction the target polynucleotide and the pseudotarget to produce a collection of amplification products that includes both a target amplicon and a pseudo target amplicon; and (4) quantifying the target amplicon without relying on information regarding the amount of pseudotarget amplicon produced in the reaction, whereby the quantity of target amplicon is related in a dose-dependent manner to the unknown amount target polynucleotide that was present in the original test sample. Amplification reactions that include a pseudo target have been shown under certain conditions to provide uniform results having less variability than similar amplification reactions lacking pseudotarget. This is particularly true for amplification of samples containing a low level of target nucleic acid. Using a pseudotarget in an amplification reaction changes the probe RLU output from an all-or-none response to a response wherein the RLU output is proportional to target input. Thus, pseudotarget allows for adjustments in assay sensitivity by changing the cutoff used to classify a sample as positive or negative, rather than re-optimizing the entire amp system to get lower sensitivity through lower amplification efficiency. Pseudotargets are further advantageous for detecting low-levels of target nucleic acid in a specimen. (See also, U.S. Pat. No. 6,294,338).

Amplification and Detection of the 16S rRNA of *A. vaginae*

For amplification and detection of sequences found in the 16S rRNA of *A. vaginae* sequences, oligomers were designed that act as amplification oligomers and detection probes by comparing known sequences of the 16S rRNA of *A. vaginae* or gene sequences encoding the 16S rRNA of *A. vaginae* and selecting sequences that are common to *A. vaginae* isolates, but preferably are not completely shared with nucleic acid sequences of other non-target species of bacteria. Sequence comparisons were conducted by using known *A. vaginae* 16S rRNA sequences (RNA or genes) of the following *Atopobium* species: *Atopobium minutum, Atopobium vaginae, Atopobium parvulum*, and *Atopobium rimae*. Specific regions were selected and the oligomers were characterized by using standard laboratory methods. Then, selected oligomer sequences were further tested by making different combinations of amplification oligomers (Table 1) and performing transcription-mediated amplification reactions comprising these amplification oligomer combinations and either synthetic *A. vaginae* 16S rRNA target sequences or *A. vaginae* 16S rRNA purified from various *Atopobium* species grown in culture. Amplification efficiencies of the *A. vaginae* 16S rRNA target sequences by the various amplification combinations were then determined. The relative efficiencies of different combinations of amplification oligomers were monitored by detecting the amplified products of the amplification reactions, generally by binding a labeled probe (Table 2) to the amplified products and detecting the relative amount of signal that indicated the amount of amplified product made. Generally, for initial testing of amplification efficiency, linear detection probes labeled with an AE compound were hybridized to the amplified products and detected by using a hybridization protection assay that selectively degrades the AE label in unhybridized probes and detects the signal from hybridized probes (substantially as described in U.S. Pat. Nos. 5,283,174, 5,656,207, 5,658,737 and 5,824,475). Preferred regions and oligomers were identified.

Embodiments of amplification oligomers for *A. vaginae* 16S rRNA sequences include those shown in Table 1. Amplification oligomers include those that may function as primer oligomers, promoter primer oligomers, and promoter provider oligomers, with promoter sequences shown in lower case in Table 1. Some embodiments are the target-specific sequence of a promoter primer oligomer listed in Table 1, which optionally may be attached to the 3' end of any known promoter sequence. One non limiting example of a promoter sequence specific for the RNA polymerase of bacteriophage T7 is SEQ ID NO:25. Preferred embodiments of amplification oligomers may include a mixture of DNA and RNA bases, and 2' methoxy linkages for the backbone joining RNA bases. Embodiments of amplification oligomers may be modified by synthesizing the oligomer as 3' blocked to make them optimal for use in a single-primer transcription-associated amplification reaction, i.e., functioning as blocking molecules or promoter provider oligomers. SEQ ID NOS:2, 9, 11, 12, 19, 27, 28, 29, 30, 31, 32, 36 & 38 in Table 1 are preferred embodiments of primer oligomers. SEQ ID NOS:3, 10, 13, 20, 35 & 37 in Table 1 are preferred embodiments of promoter primer oligomers. Promoter regions of SEQ ID NOS:3, 10, 13, 20, 35 & 37 are shown in lowercase lettering; target-binding regions are shown in uppercase lettering. SEQ ID NOS:27, 28, 29, 30, 36 & 38 of Table 1 are the target binding regions of SEQ ID NOS:3, 10, 13, 20, 35 & 37, respectively. SEQ ID NOS:27, 28, 29, 30, 36 & 38 can be used as second primer members of an amplification oligomer combination, or can be joined with promoter sequences, as described, to form promoter primers or promoter providers if 3'blocked.

FIGS. 2A-B are an exemplary amplification oligomer combination (SEQ ID NOS:2 & 27) and a resultant amplicon (SEQ ID NO:43) In these illustrations, the amplification oligomer combination comprises two primer oligomer members. In amplification oligomer combinations wherein a promoter primer is used, the amplicon will incorporate the non-target-specific promoter sequence, thus comprising a target-specific sequence and a non-target-specific sequence. For example, SEQ ID NO:3 is a promoter primer targeting the same nucleic acids of *A. vaginae* as does SEQ ID NO:27, but SEQ ID NO:3 further comprises a promoter sequence. A resultant amplicon from a SEQ ID NOS:2 & 3 amplification oligomer combination reaction will incorporate the non-target specific promoter sequence and the target specific sequence, illustrated as SEQ ID NO:43.

TABLE 1

*A. vaginae* Amplification Oligomer Sequences

| Sequence 5'→3' | SEQ ID NO. |
|---|---|
| CTTTCAGCAGGGACGAGG | 2 |
| GGATTAGATACCCTGGTAGTCC | 9 |
| ACTGAGACACGGCCCAAACTCCTACGGGAGG | 11 |
| ACTCCTACGGGAGGCAGCAGTAG | 12 |
| AAGTGGCGAACGGCTGAGTAA | 19 |
| aatttaatacgactcactatagggagaTATCAGGAGCGGATAGGGGTTGA | 3 |
| TATCAGGAGCGGATAGGGGTTGA | 27 |
| aatttaatacgactcactatagggagaCCCGTCAATTCCTTTGAG | 10 |
| CCCGTCAATTCCTTTGAG | 28 |
| aatttaatacgactcactatagggagaTTACCGCGGCTGCTGGCACG | 13 |
| TTACCGCGGCTGCTGGCACG | 29 |
| aatttaatacgactcactatagggagaATCATTGCCTTGGTAGGCC | 20 |
| ATCATTGCCTTGGTAGGCC | 30 |
| GTGGCGAACGGCTGAGTAACAC | 31 |
| AACGGCTGAGTAACACGTG | 32 |
| aatttaatacgactcactatagggagaGGAGTATCCGGTATTAACCTCGG | 35 |
| GGAGTATCCGGTATTAACCTCGG | 36 |
| aatttaatacgactcactatagggagaGGAGTATCCGGTATTAACCTC | 37 |
| GGAGTATCCGGTATTAACCTC | 38 |
| aatttaatacgactcactatagggaga | 25 |

Embodiments of detection probe oligomers for amplified products of *A. vaginae* 16S rRNA sequences or genes encoding *A. vaginae* 16S rRNA are shown in Table 2. Preferred embodiments of linear detection probe oligomers are labeled with a chemiluminescent AE compound which is attached to the probe sequence via a linker (substantially as described in U.S. Pat. Nos. 5,585,481 and 5,639,604, particularly at column 10, line 6 to column 11, line 3, and in Example 8). Examples of preferred labeling positions are a central region of the probe oligomer and near a region of A:T base pairing, at a 3' or 5' terminus of the oligomer, and at or near a mismatch site with a known sequence that is not the desired target sequence. Examples of preferred embodiments of such AE-labeled oligomers include those with a linker between: residues 10 and 11 of SEQ ID NO:4, residues 14 and 15 of SEQ ID NOS:14 & 33, residues 15 and 16 of SEQ ID NO:15, residues 9 and 10 of SEQ ID NO:16, residues 11 and 12 of SEQ ID NO:17, residues 12 and 13 of SEQ ID NO:18, and residues 7 and 8 of SEQ ID NO:34. Detection probes may be used with helper probes that are unlabeled and facilitate binding of the labeled probe to its target as previously described (U.S. Pat. No. 5,030,557, Hogan et al.). FIG. 2C illustrates the use of a detection oligomer for detecting an amplicon (in this illustration, SEQ ID NO:43).

TABLE 2

*A. vaginae* Detection Probe Oligomer Sequences

| Sequence | SEQ ID NO. |
|---|---|
| GGUCAGGAGUUAAAUCUGG | 4 |
| TCAGCAGGGACGAGGCCGCAAGGTGA | 14 |
| GTTAGGTCAGGAGTTAAATCTGG | 15 |
| CGGTCTGTTAGGTCAGGAGTT | 16 |
| GGTCAGGAGTTAAATCTGG | 17 |
| CCGAGGTTAATACCGGATACTC | 18 |
| GGCAACCTGCCCTTTGCACTGGGATA | 33 |
| TGCCCTTTGCACTGGGATAGCCTCGGGA | 34 |

Embodiments of capture probe oligomers for use in sample preparation to separate *A. vaginae* 16S rRNA target nucleic acids from other sample components include those that contain the target-specific sequences of SEQ ID NO:21 (CTACTGCTGCCTCCCGTAGGAG), SEQ ID NO:22 (GGACTACCAGGGTATCTAATCCTG), SEQ ID NO:23 (CGACACGAGCTGACGACAGCCATGCA), SEQ ID NO:24 (GACGTCATCCCCACCTTCCT), SEQ ID NO:40 (CCACCAACTAGCTAACAGG), and SEQ ID NO:42 (AACCCGGCTACCCATCATTGCCTTGG). Preferred embodiments of the capture probes include a 3' tail region covalently attached to the target-specific sequence to serve as a binding partner that binds a hybridization complex made up of the target nucleic acid and the capture probe to an immobilized probe on a support. Preferred embodiments of capture probes that include the target-specific sequences of SEQ ID NOS:21, 22, 23, 24, 40 & 42, further include 3' tail regions made up of substantially homopolymeric sequences, such as $dT_3A_{30}$ polymers. One particularly preferred embodiment of capture probes includes: SEQ ID NOS:5, 6, 7, 8, 39 & 41.

Reagents used in target capture, amplification and detection steps in the examples described herein generally include one or more of the following. Sample Transport Solution contained 15 mM sodium phosphate monobasic, 15 mM sodium phosphate dibasic, 1 mM EDTA, 1 mM EGTA, and 3% (w/v) lithium lauryl sulfate (LLS), at pH 6.7. Lysis buffer contained 790 mM HEPES, 230 mM succinic acid, 10% (w/v) LLS, and 680 mM lithium hydroxide monohydrate. Specimen Dilution Buffer contained 300 mM HEPES, 3% (w/v) LLS, 44 mM LiCl, 120 mM LiOH, 40 mM EDTA, at pH 7.4. Target Capture Reagent contained 250 mM HEPES, 310 mM lithium hydroxide, 1.88 M lithium chloride, 100 mM EDTA, at pH 6.4, and 250 µg/ml of paramagnetic particles (0.7-1.05µ particles, SERA-MAG™ MG-CM, Seradyn, Inc., Indianapolis, Ind.) with $(dT)_{14}$ oligomers covalently bound thereto. Wash Solution used in target capture contained 10 mM HEPES, 150 mM NaCl, 6.5 mM NaOH, 1 mM EDTA, 0.3% (v/v) ethanol, 0.02% (w/v) methyl paraben, 0.01% (w/v) propyl paraben, and 0.1% (w/v) sodium lauryl sulfate, at pH 7.5. Amplification reagent was a concentrated mixture that was mixed with other reaction components (e.g., sample or specimen dilution components) to produce a mixture containing 47.6 mM Na-HEPES, 12.5 mM N-acetyl-L-cysteine, 2.5% TRITON™ X-100, 54.8 mM KCl, 23 mM $MgCl_2$, 3 mM NaOH, 0.35 mM of each dNTP (dATP, dCTP, dGTP, dTTP), 7.06 mM rATP, 1.35 mM rCTP, 1.35 mM UTP, 8.85 mM rGTP, 0.26 mM $Na_2EDTA$, 5% v/v glycerol, 2.9% trehalose, 0.225% ethanol, 0.075% methylparaben, 0.015% propylparaben, and 0.002% Phenol Red, at pH 7.5-7.6. Amplification oligomers (primers, promoter primers, blocker oligomers, promoter provider oligomers), and optionally probes, may be added to the reaction mixture in the amplification reagent or separate from the amplification reagent. Enzymes were added to TMA reaction mixtures at about 90 U/µl of MMLV reverse transcriptase (RT) and about 20 U/µl of T7 RNA polymerase per reaction (1 U of RT incorporates 1 nmol of dTTP in 10 min at 37.degree.C. using 200-400 micromolar oligo dT-primed polyA template, and 1 U of T7 RNA polymerase incorporates 1 nmol of ATP into RNA in 1 hr at 37.degree.C. using a T7 promoter in a DNA template). Probe Reagent that contained AE-labeled detection probes was a solution made up of either (a) 100 mM lithium succinate, 3% (w/v) LLS, 10 mM mercaptoethanesulfonate, and 3% (w/v) polyvinylpyrrolidon, or (b) 100 mM lithium succinate, 0.1% (w/v) LLS, and 10 mM mercaptoethanesulfonate. Hybridization Reagent for AE-labeled probe binding to target nucleic acids was made up of 100 mM succinic acid, 2% (w/v) LLS, 100 mM lithium hydroxide, 15 mM aldrithiol-2, 1.2 M lithium chloride, 20 mM EDTA, and 3.0% (v/v) ethanol, at pH 4.7. Selection Reagent for preferentially hydrolyzing an AE label on unbound detection probes contained 600 mM boric acid, 182.5 mM NaOH, 1% (v/v) octoxynol (TRITON® X-100) at pH 8.5. Detection Reagents for producing a chemiluminescent response from AE labels comprised Detect Reagent I (1 mM nitric acid and 32 mM $H_2O_2$), and Detect Reagent II (1.5 M NaOH) to neutralize the pH (as in U.S. Pat. Nos. 5,283,174, 5,656,744, and 5,658,737). All of the reagent addition and mixing steps may be performed manually, using a combination of manual and automated steps, or by using a completely automated system. The transcription mediated amplification (TMA) reactions use substantially the procedures as disclosed in U.S. Pat. Nos. 5,399,491 and 5,554,516, Kacian et al., which are incorporated by reference herein. The amplification methods that use single-primer transcription associated amplification substantially use the procedures already disclosed in detail in U.S. Pat. No. 5,399,491 to Kacian et al. and U.S. Pat. No. 7,374,885 to Becker et al., the details of which are incorporated by reference herein. The use and detection of signal from AE-labeled probes to detect hybridization complexes with target sequences use the procedures already disclosed in detail in U.S. Pat. Nos. 5,283,174 and 5,656,744, Arnold et al., and U.S. Pat. No. 5,658,737, Nelson et al., the details of which are incorporated by reference herein.

By using various combinations of these amplification oligomers and AE-labeled detection probes to provide a detectable chemiluminescent signal, A. vaginae 16S rRNA sequences were specifically detected when the sample contained about 100 copies of the A. vaginae 16S rRNA target sequence. Some preferred amplification oligomer combinations are SEQ ID NOS:2 & 3; and SEQ ID NOS:2 & 27. A particularly preferred amplification oligomer combination is SEQ ID NOS: 2 & 3. Some preferred combinations of amplification and detection oligomers include SEQ ID NOS: 2, 3 & 4; SEQ ID NOS:2, 3 & 15; SEQ ID NOS:2, 3 & 16; SEQ ID NOS:2, 3 & 17; SEQ ID NOS:2, 27 & 4; SEQ ID NOS:2, 27 & 15; SEQ ID NOS:2, 27 & 16; and SEQ ID NOS:2, 27 & 17. A particularly preferred amplification and detection oligomer combination is SEQ ID NOS:2, 3 & 4. Setting a cut-off value at 50,000 RLUs, this particularly preferred amplification and detection oligomer combination showed a sensitivity down to as few as 1000 CFU per reaction of A. vaginae when using as little as 20 pM/reaction of each amplification oligomer. Setting an RLU cut-off value of 100,000, the preferred amplification and detection oligomer combination showed a sensitivity down to as few as 10,000 CFU per reaction of A. vaginae when using as little as 10 pM/reaction of each amplification oligomer.

Detecting A. vaginae to diagnosis bacterial vaginosis in a clinical sample will preferably use higher RLU cut-off values than those used for detecting the presence/absence of A. vaginae from a sample. This is because for diagnosis of BV, normal samples can be positive for relatively low amounts of A. vaginae while BV samples will have relatively greater amounts of A. vaginae. So for diagnosis, a higher RLU cut-off value is one approach to differentiating normal levels of A. vaginae from elevated levels present in a sample. Depending on the desired application for the amplification and detection oligomers described herein, a skilled artisan will set an appropriate RLU cut-off value, with lower values being useful for detecting all A. vaginae present in a sample, and higher RLU values being useful for detecting a threshold amount of A. vaginae in a sample.

Additional microbe detection assays can be similarly performed for determining the presence and/or relative amount of a plurality of microbes implicated in BV. By way of example only, such plurality of microbes can include one or more of anaerobic gram-positive cocci; Megasphaera sp.; Lactobacillus sp.; Lactobacillus iners; Lactobacillus crispatus group; Lactobacillus gasseri group; Gardnerella sp; Gardnerella vaginalis; Trichamonas sp; Trichamonas vaginalis; Candida sp; Eggerthella sp.; Bacterium from the order Clostridiales; Clostridium-like sp.; Prevotella sp.; Prevotella bivia group; Prevotella buccalis group; Atopobium sp.; Atopobium vaginae; Enterobacteria; Peptostreptococcus micros; Aerococcus christensenii; Leptotrichia amnionii; Peptoniphilus sp.; Dialister sp.; Mycoplasma hominis; Sneathia sanguinegens; Anaerococcus tetradius; Mobiluncus sp.; Mobiluncus hominis; Eggerthella hongkongensis; Megasphaera sp; Leptotrichia sanguinegens and Finegoldia magna. Assays may be performed separately or multiplexed. Thus, a diagnosis of BV can include identifying a plurality of microbes and optionally determining their relative abundances in a sample.

The following examples illustrate some of the embodiments of the invention for detection of A. vaginae 16S rRNA target sequences.

Example 1

Amplification Oligomer Titration with *A. vaginae* 16S rRNA Target

In this example, known numbers of *A. vaginae* 16S rRNA sequences from *A. vaginae* were amplified in TMA reactions using primer SEQ ID NO:2 and promoter primer SEQ ID NO:3 amplification oligomers. The amplified products were detected by using the probe oligomer SEQ ID NO:4 labeled with AE between nt 10 and 11 of the detection oligomer probe sequence. An initial target capture step was performed using SEQ ID NOS:5 & 6 oligomers.

Briefly, target specimens were prepared by serially diluting a stock supply of *A. vaginae* cells obtained from American Type Cell Culture (Manassas, Va. Cat No. BAA-55). The stock supply was 1.25 E6 CFU/mL of *A. vaginae* and was diluted to 100,000, 10,000, 1,000, 100 and 0 CFU/mL using dilution buffer. *A. vaginae* cells were lysed using lysis buffer and incubating at 95.degree.C. for 10 minutes. Lysis buffer also protected the released target RNA from RNase degradation. *A. vaginae* target rRNA was isolated from the lysis buffer using target capture oligomers and a magnetic bead procedure as is generally described. Amplification oligomers SEQ ID NOS:2-3 were then tested against each of these target dilution amounts using four concentrations of oligomers; 40 pM/reaction each, 30 pM/reaction each, 20 pM/reaction each and 10 pM/reaction each. Five replications of each reaction condition were assayed by TMA and hybridization protection assay using an SB100 Dry Heat Bath/Vortexer (Gen-Probe Incorporated, San Diego, Calif. Cat #5524). Reaction wells containing target dilution were mixed with amplification reagent and one of the various concentrations of amplification oligomers. Blank reaction wells containing oligomerless amplification reagent were included for each reaction condition. Reaction wells were amplified in a TMA reaction using substantially the procedures described previously in detail (U.S. Pat. Nos. 5,399,491 and 5,554,516, Kacian et al.). Briefly, the reaction mixture (about 0.08 ml) containing amplification reagent, target nucleic acid, and amplification oligomers was mixed, covered with silicon oil (0.2 ml) to prevent evaporation, and incubated for 10 min at 62.degree.C. and then for 5 min at 42.degree.C., and then the enzyme reagent (0.025 ml containing reverse transcriptase and T7 RNA polymerase) was added, and the reaction mixtures were incubated for 60 min at 42.degree.C.

Following amplification, detection of the amplified products involved mixing the amplification mixture with a labeled detection probe oligomer of SEQ ID NO:4 in an amount determined to produce a maximum detectable signal of about 5,000,000 relative light units ("RLU") from the hybridized labeled probe). The mixtures of probe and amplified sequences were treated to bind the probe to the amplified product and detect the chemiluminescent signal produced from hybridized probes substantially as described previously (U.S. Pat. Nos. 5,283,174 and 5,639,604, Arnold Jr. et al.). Briefly, the probe and amplified product mixtures were incubated for 20 min at 62.degree.C., then cooled at room temperature for about 5 min and selection reagent (0.25 ml) was added, mixed, and incubated 10 min at 62.degree.C. followed by room temperature for 15 min to hydrolyze the label on unbound probes. Chemiluminescent signal from AE on bound probes was produced by adding detect reagent I, incubating, adding detect reagent II, and detecting by measuring RLU using a luminometer (e.g., LEADER®, Gen-Probe Incorporated, San Diego, Calif.). The results of these assays are shown below as the range and average RLU for five assays performed on each of the amplification oligomer conditions shown. In all cases, negative controls (reaction wells containing 0 CFU/mL of target) provided a background signal of between 734 and 1,055 RLU. Blank wells provided a signal of between 15 and 22 RLU. As few as 10 pM/reaction of amplification oligomers SEQ ID NOS:2 & 3 in a TMA reaction were able to amplify as few as 100 CFU/mL of *A. vaginae* 16S rRNA target sequence to produce a detectable signal with AE-labeled probe of SEQ ID NO:4. (See Table 3). These results show that increasing amplification oligomer concentration corresponded to an increasing RLU signal over the various CFU/mL of *A. vaginae* cell input.

TABLE 3

Amplification Oligomer Titration Results

| Target Source CFU/mL | | Amp. oligos 10 pM/rxn each RLU range (RLU Avg: sd) | Amp. oligos 20 pM/rxn each RLU range (RLU Avg: sd) | Amp. oligos 30 pM/rxn each RLU range (RLU Avg: sd) | Amp. oligos 40 pM/rxn each RLU range (RLU Avg: sd) |
|---|---|---|---|---|---|
| BAA-55 | 0 | 824-887 (867: 25) | 935-1055 (983: 48) | 805-943 (877: 62) | 734-826 (768: 38) |
| BAA-55 | 100 | 1261-1680 (1525: 166) | 4153-19063 (7776: 6412) | 10343-11784 (11228: 600) | 24193-40979 (30569: 6776) |
| BAA-55 | 1000 | 6716-12221 (9816: 2030) | 42096-66488 (54164: 10452) | 80957-132772 (98157: 20929) | 88752-564608 (412606: 190870) |
| BAA-55 | 10000 | 84338-105007 (94746: 9091) | 445534-1982936 (802197: 660964) | 586845-1773054 (1272793: 436813) | 3749552-4380873 (3854572: 316272) |
| BAA-55 | 100000 | 391920-880748 (681437: 198212) | 4654952-6285906 (5561972: 641195) | 4704282-6477956 (6050155: 757582) | 6421967-6977231 (6623206: 232342) |
| Blank | | 16-22 (19.6) | 16-21 (18.6) | 16-19 (17) | 15-19 (16.6) |

Example 2

Varied Amplification Oligomer Concentrations

In this example, 10,000 CFU/mL of *A. vaginae* cells from a stock supply was amplified in a TMA reaction using varied amplification oligomer concentrations. Primer SEQ ID NO:2 was tested at 3.8, 10, 25, 40 & 46.2 pM/mL. Promoter primer SEQ ID NO:3 was tested at 3.8, 10, 25, 40 & 46.2 pM/mL. An initial target capture step was performed using target capture oligomers SEQ ID NOS:5-6. Amplicon detection was performed using detection probe SEQ ID NO:4.

A stock supply of A. vaginae cells at 1.25 E6 CFU/mL was diluted to 10,000 CFU/mL. Cells were lysed using lysis buffer and the target nucleic acids were isolated using a magnetic bead target capture procedure. Isolated nucleic acids were then added to five reaction wells for each amplification oligomer condition tested. Nine amplification oligomer conditions were prepared as follows (SEQ ID NO:2-SEQ ID NO:3): 10 pM/rxn-10 pM/rxn; 10 pM/rxn-40 pM/rxn; 40 pM/rxn-10 pM/rxn; 40 pM/rxn-40 pM/rxn; 25 pM/rxn-3.8 pM/rxn; 25 pM/rxn-46.2 pM/rxn; 3.8 pM/rxn-25 pM/rxn; 46.2 pM/rxn-25 pM/rxn; and 25 pM/rxn-25 pM/rxn. An additional 5 reaction wells having 0 CFU of A. vaginae cells, 40 pM/rxn of SEQ ID NO:2 and 40 pM/rxn of SEQ ID NO:3 were prepared as negative control.

The reactions were performed using a TMA and hybridization protection assay, as discussed. Reaction wells containing target nucleic acids from 10,000 CFU/mL of A. vaginae cells were mixed with amplification reagent and one of the amplification oligomer conditions. Reaction wells from the 0 CFU negative control were mixed with amplification reagent and 40 pM/rxn of each of SEQ ID NOS:2-3. Reaction wells were then amplified in a TMA reaction as generally described. Following amplification, detection of the amplified products was performed as described using a labeled detection probe oligomer of SEQ ID NO:4. The mixtures of probe and amplicon were incubated for 20 min at 62.degree.C., then cooled at room temperature for about 5 min and selection reagent (0.25 ml) was added, mixed, and incubated 10 min at 62.degree.C. followed by room temperature for 15 min to hydrolyze the label on unbound probes. Chemiluminescent signal from AE on bound probes was produced by adding detect reagent I, incubating, adding detect reagent II, and detecting by measuring RLU using a LEADER® luminometer. The results of these assays are shown below in Table 4. In this assay RLU increases correspond more closely with increases in the primer oligomer concentration than with increases in the promoter primer concentration.

TABLE 4

Amplification Oligomer Concentration Results

| CFU input | SEQ ID NO: 2-SEQ ID NO3 | Average RLU (SD) | Range RLU |
|---|---|---|---|
| 0 | 40-40 | 798 | 725-962 |
| 10,000 | 10-10 | 212,697 (123,007) | 74,635-393,066 |
| 10,000 | 10-40 | 309,104 (153,575) | 45,279-395,736 |
| 10,000 | 40-10 | 4,130,915 (1,053,463) | 3,103,942-5,898,362 |
| 10,000 | 40-40 | 5,220,384 (678,104) | 4,375,509-5,965,335 |
| 10,000 | 25-3.8 | 614,797 (217,518) | 298,186-849,483 |
| 10,000 | 25-46.2 | 1,621,922 (794,882) | 249,806-2,278,124 |
| 10,000 | 3.8-25 | 25,453 (3,903) | 20,082-30,796 |
| 10,000 | 46.2-25 | 6,118,494 (326,660) | 5,796,174-6,618,642 |
| 10,000 | 25-25 | 2,206,064 (178,637) | 1,960,679-2,368,017 |

Example 3

Sensitivity Testing of Amplification Oligomers to A. vaginae Target Nucleic Acid To provide sample conditions similar to those from clinical specimen, vaginal swabs were collected from subjects shown to be negative for A. vaginae using the above detection compositions and methods. The negative specimens were randomly separated into two groups and each group was pooled in Sample Transport Solution. The pooled specimens were then further separated and were spiked with 0, 100, 1,000, 10,000 or 100,000 CFU/mL of A. vaginae cells from stock sample. Following incubation in lysis buffer and isolation of nucleic acids using target capture oligomers and magnetic bead separation, the target nucleic acids were amplified and detected.

Each condition for the two pools were then amplified in triplicate using SEQ ID NOS 2-3 amplification oligomers followed by detection using SEQ ID NO:4 detection probe. The amplification reaction proceeded as is generally described herein using TMA, hybridization protection and SB100 platform, as generally described herein. Reaction wells containing target nucleic acids from 0, 100, 1,000, 10,000 or 100,000 CFU/mL of A. vaginae cells were mixed with amplification reagent and the amplification oligomers. The SEQ ID NO:2 primer oligomer was at a 50 pM/rxn concentration and the SEQ ID NO:3 promoter primer oligomer was at a 20 pM/rxn concentration. Blank wells containing neither A. vaginae cells nor amplification oligomers (oligoless amplification reagent only) were also included in the reaction. Reaction wells were then amplified in a TMA reaction as generally described. Detection of the amplified products was performed using a labeled detection probe oligomer of SEQ ID NO:4. The mixtures of probe and amplicon were incubated for 20 min at 62.degree.C., cooled at room temperature for about 5 min, and selection reagent (0.25 ml) was added, mixed, and incubated 10 min at 62.degree.C. followed by room temperature for 15 min to hydrolyze the label on unbound probes. Chemiluminescent signal from AE on bound probes was produced by adding detect reagent I, incubating, adding detect reagent II, and detecting by measuring RLU using a LEADER® luminometer. The results of these assays are shown below in Table 5.

TABLE 5

Amplification Oligomer Sensitivity

| Conditions | | | |
|---|---|---|---|
| Pool # | CFU | Avg RLU (SD) | RLU Range |
| Blank | Blank | 18 | 16-19 |
| 1 | 0 | 905 (91) | 786-1,015 |
| 1 | 100 | 5,436 (562) | 4,843-5,960 |
| 1 | 1,000 | 47,080 (1,295) | 45,823-48,409 |
| 1 | 10,000 | 445,808 (88,062) | 373,967-544,051 |
| 1 | 100,000 | 4,340,659 (121,451) | 4,200,897-4,400,520 |
| Blank | Blank | 20 | 17-23 |
| 2 | 0 | 928 (50) | 890-1,015 |
| 2 | 100 | 3,892 (391) | 3,562-4,324 |
| 2 | 1,000 | 25,600 (713) | 24,809-26,194 |
| 2 | 10,000 | 258,231 (23,520) | 243,689-285,366 |
| 2 | 100,000 | 2,316,486 (233,864) | 2,063,622-2,524,998 |

From these data, the A. vaginae amplification and detection oligomers are sensitive to 10,000 CFU/mL. A. vaginae bacterium is reportedly present at low levels in about 10% of normal (non-bacterial vaginosis) specimen. In bacterial vaginosis, the levels of A. vaginae are reportedly much higher than normal levels. Thus, depending on the objective of an amplification and detection assay, the RLU cut-off can be adjusted. For example, for detecting all A. vaginae in a specimen a low RLU cut-off can be used, whereas, detecting levels of A. vaginae that indicate bacterial vaginosis disorder can use higher RLU values.

Example 4

Specific Amplification and Detection of *A. vaginae* Target Sequences

TMA reactions were performed on two cross-reactivity panels of organisms using amplification oligomers of SEQ ID NOS:2-3, and an AE-labeled detection probe of SEQ ID NO:4 (100 fmol per reaction). The cross-reactivity panels included the non-target organisms shown in Table 6, and were tested at 1,000,000 or 10,000,000 CFU per reaction. Also tested were 100, 1,000 and 10,000 CFU/reaction of *A. vaginae* cells. Nucleic acids were prepared as generally described herein. Following incubation in lysis buffer and isolation of nucleic acids using target capture oligomers and magnetic bead separation, the target nucleic acids were amplified and detected.

Each of the *A. vaginae* cell concentrations and the cross-reactivity panel organism cells were tested in five reaction wells using SEQ ID NOS 2-3 amplification oligomers followed by detection using SEQ ID NO:4 detection probe. The amplification reaction proceeded as is generally described herein using TMA, hybridization protection and the SB100 platform, as generally described herein. Reaction wells containing target nucleic acids from *A. vaginae* cells or from cross-reactivity panel organism cells were mixed with amplification reagent and the amplification oligomers. The SEQ ID NO:2 primer oligomer was at a 50 pM/rxn concentration and the SEQ ID NO:3 promoter primer oligomer was at a 20 pM/rxn concentration. Reaction wells were then amplified in a TMA reaction as generally described. Detection of the amplified products was performed using a labeled detection probe oligomer of SEQ ID NO:4. The mixtures of probe and amplicon were incubated for 20 min at 62.degree.C., cooled at room temperature for about 5 min, and selection reagent (0.25 ml) was added, mixed, and incubated 10 min at 62.degree.C. followed by room temperature for 15 min to hydrolyze the label on unbound probes. Chemiluminescent signal from AE on bound probes was produced by adding detect reagent I, incubating, adding detect reagent II, and detecting by measuring RLU using a LEADER® luminometer. The results of these assays are shown below in Table 6. A positive criterion was set as an RLU value of 100,000 or greater. No cross-reactivity was observed.

TABLE 6

Cross-Reactivity Testing of an *A. vaginae* Amplification Oligomer and Detection Oligomer Set.

| Conditions | | AVG RLU | |
| --- | --- | --- | --- |
| Organism | CFU/rxn | (sd) | RLU Range |
| Blank | Blank | 17.6 (2.1) | 15-20 |
| A vaginae | 0 | 621 (59) | 524-683 |
| A vaginae | 100 | 67954 (44641) | 19567-112348 |
| A vaginae | 1,000 | 1043173 (1091270) | 402270-2979096 |
| A vaginae | 10,000 | 3868010 (2075163) | 162638-4973895 |
| Neisseria meningitidis serogroup A | 1,000,000 | 623 (79) | 554-752 |
| Neisseria meningitidis serogroup B | 1,000,000 | 663 (88) | 598-810 |
| Neisseria meningitidis serogroup C | 1,000,000 | 605 (38) | 573-670 |
| Neisseria meningitidis serogroup D | 1,000,000 | 728 (194) | 604-1059 |

TABLE 6-continued

Cross-Reactivity Testing of an *A. vaginae* Amplification Oligomer and Detection Oligomer Set.

| Conditions | | AVG RLU | |
| --- | --- | --- | --- |
| Organism | CFU/rxn | (sd) | RLU Range |
| Giardia intestinalis | 1,000,000 | 701 (131) | 538-854 |
| Ureaplasma urealyticum | 1,000,000 | 619 (16) | 610-648 |
| Mycoplasma genitalium | 1,000,000 | 629 (44) | 589-693 |
| Candida albicans | 1,000,000 | 605 (16) | 585-621 |
| Candida glabrata | 1,000,000 | 637 (15) | 613-655 |
| Candida parapsilosis | 1,000,000 | 610 (16) | 596-636 |
| Candida tropicalis | 1,000,000 | 694 (109) | 592-851 |
| Escherichia coli | 1,000,000 | 663 (28) | 631-704 |
| Gardnerella vaginalis | 1,000,000 | 614 (43) | 549-666 |
| Staphylococcus aureus | 1,000,000 | 648 (79) | 605-787 |
| Staphylococcus epidermidis | 1,000,000 | 653 (76) | 576-772 |
| Lactobacillus acidophilus | 1,000,000 | 727 (88) | 708-877 |
| Lactobacillus brevis | 1,000,000 | 709 (54) | 668-803 |
| Lactobacillus jensenii | 1,000,000 | 703 (67) | 654-818 |
| Lactobacillus lactis | 1,000,000 | 666 (29) | 638-712 |
| Kingella kingae | 10,000,000 | 615 (20) | 587-637 |
| Neisseria cinerea | 10,000,000 | 672 (29) | 647-719 |
| Neisseria elongata | 10,000,000 | 631 (21) | 607-652 |
| Neisseria flava | 10,000,000 | 654 (37) | 610-707 |
| Neisseria flavescens | 10,000,000 | 627 (45) | 559-682 |
| Neisseria lactamica | 10,000,000 | 650 (21) | 615-664 |
| Neisseria meningitidis serogroup W135 | 10,000,000 | 678 (40) | 637-740 |
| Neisseria meningitidis serogroup Y | 10,000,000 | 693 (37) | 664-755 |
| Neisseria mucosa | 10,000,000 | 619 (31) | 582-648 |
| Neisseria polysaccharea | 10,000,000 | 700 (29) | 656-726 |
| Neisseria sicca | 10,000,000 | 627 (21) | 608-659 |
| Neisseria subflava | 10,000,000 | 676 (56) | 628-747 |
| Neisseria gonorrhoeae | 10,000,000 | 643 (28) | 597-672 |
| Moraxella osloensis | 10,000,000 | 800 (192) | 654-1066 |
| Derxia gummosa | 10,000,000 | 750 (63) | 705-856 |
| Enterococcus faecalis | 10,000,000 | 732 (134) | 619-964 |

For the *A. vaginae* cells tested, 2 of 5 replicates were positive at 100 CFU per reaction and 5 of 5 replicates were positive at 1,000 and 10,000 CFU per reaction. For the non-target organisms tested in the cross-reactivity panels, none were found to be positive (100,000 RLU or greater). No cross-reactivity was found with any of the non-target organisms tested.

Example 5

Amplification and Detection of *A. vaginae* in Samples Containing Pseudotarget A series of TMA reactions containing pseudotarget can be prepared using amplification oligomers specific for a segment of the *A. vaginae* 16S rRNA. (e.g., SEQ ID NOS:2 & 3). One example of a pseudotarget useful with these amplification oligomers is SEQ ID NO:26 (5'-CTTTCAGCAGGGACGAGGCTCAACCCC-TATCCGCTCCTGATA-3'). Each reaction can receive a known amount of *A. vaginae* 16S rRNA. For example, the 1.25 E6 CFU/mL of stock *A. vaginae* can be diluted to 100,000, 10,000, 1,000, 100 and 0 CFU/mL using specimen buffer. In this example, these reactions can also included either 0, $10^5$, $10^6$ or $10^7$ copies of the SEQ ID NO:26 pseudotarget. Amplification reagent containing the SEQ ID NOS:2 & 3 amplification oligomers can then be added and the reaction can be incubated first at 65.deg.C. for 10 minutes to allow amplification oligomer-target annealing, and then at 42.deg.C. for an additional 5 minutes. Thereafter, each reaction can receive enzyme mixture containing reverse transcriptase and T7 RNA polymerase. Reactions can then be incubated at 42.deg.C. for an additional 60 minutes. Thereafter, samples of the reaction mixtures can be combined with probe reagent, containing probe (e.g., SEQ ID NO:4) bearing an acridinium ester moiety as the label. The sequence of the probe preferably permits hybridization through complementary base pairing only with the target amplicon and not with the pseudotarget amplicon. After hybridizing the mixture at 60.deg.C. for 15 minutes, 300.micro·l of selection reagent can be added and the mixture incubated at 60.deg.C. to inactivate unhybridized probe. Finally, the mixtures can be cooled to room temperature, placed into a luminometer and the amount of analyte amplicon quantitated by measuring the light emitted from a chemiluminescent reaction (in RLUs). Briefly, each reaction tube can be injected first with detection reagent I, then with detection reagent II in order to stimulate light emission. Results will quantitatively indicated the amount of amplicon produced in different reactions, and the variability of these results will be decreased as the amount of pseudotarget is optimized for the reaction.

TABLE 7

Exemplary Oligomers, Reference Sequences and Regions.

| SEQ ID NO: | Sequence (5' to 3') |
|---|---|
| 1 | (See, FIG.1 and GenBank Accession No. AF325325.1 GI:12240234, entered Jan. 16, 2001) |
| 2 | CTTTCAGCAGGGACGAGG |
| 3 | AATTTAATACGACTCACTATAGGGAGATATCAGGAGCGGATAGGGGTTGA |
| 4 | GGUCAGGAGUUAAAUCUGG |
| 5 | CTACTGCTGCCTCCCGTAGGAGTTTAAAAAAAAAAAAAAAAAAAAAAAAAAAAA |
| 6 | GGACTACCAGGGTATCTAATCCTGTTTAAAAAAAAAAAAAAAAAAAAAAAAAAAA |
| 7 | CGACACGAGCTGACGACAGCCATGCATTTAAAAAAAAAAAAAAAAAAAAAAAAAAAA |
| 8 | GACGTCATCCCCACCTTCCTTTTAAAAAAAAAAAAAAAAAAAAAAAAAAA |
| 9 | GGATTAGATACCCTGGTAGTCC |
| 10 | AATTTAATACGACTCACTATAGGGAGACCCGTCAATTCCTTTGAG |
| 11 | ACTGAGACACGGCCCAAACTCCTACGGGAGG |
| 12 | ACTCCTACGGGAGGCAGCAGTAG |
| 13 | AATTTAATACGACTCACTATAGGGAGATTACCGCGGCTGCTGGCACG |
| 14 | TCAGCAGGGACGAGGCCGCAAGGTGA |
| 15 | GTTAGGTCAGGAGTTAAATCTGG |
| 16 | CGGTCTGTTAGGTCAGGAGTT |
| 17 | GGTCAGGAGTTAAATCTGG |
| 18 | CCGAGGTTAATACCGGATACTC |
| 19 | AAGTGGCGAACGGCTGAGTAA |
| 20 | AATTTAATACGACTCACTATAGGGAGAATCATTGCCTTGGTAGGCC |
| 21 | CTACTGCTGCCTCCCGTAGGAG |
| 22 | GGACTACCAGGGTATCTAATCCTG |
| 23 | CGACACGAGCTGACGACAGCCATGCA |
| 24 | GACGTCATCCCCACCTTCCT |
| 25 | aatttaatacgactcactatagggaga |
| 26 | CTTTCAGCAGGGACGAGGCTCAACCCCTATCCGCTCCTGATA |
| 27 | TATCAGGAGCGGATAGGGGTTGA |
| 28 | CCCGTCAATTCCTTTGAG |
| 29 | TTACCGCGGCTGCTGGCACG |
| 30 | ATCATTGCCTTGGTAGGCC |

TABLE 7-continued

Exemplary Oligomers, Reference Sequences and Regions.

| SEQ ID NO: | Sequence (5' to 3') |
|---|---|
| 31 | GTGGCGAACGGCTGAGTAACAC |
| 32 | AACGGCTGAGTAACACGTG |
| 33 | GGCAACCTGCCCTTTGCACTGGGATA |
| 34 | TGCCCTTTGCACTGGGATAGCCTCGGGA |
| 35 | AATTTAATACGACTCACTATAGGGAGAGGAGTATCCGGTATTAACCTCGG |
| 36 | GGAGTATCCGGTATTAACCTCGG |
| 37 | AATTTAATACGACTCACTATAGGGAGAGGAGTATCCGGTATTAACCTC |
| 38 | GGAGTATCCGGTATTAACCTC |
| 39 | CCACCAACTAGCTAACAGGTTTAAAAAAAAAAAAAAAAAAAAAAAAAAAA |
| 40 | CCACCAACTAGCTAACAGG |
| 41 | AACCCGGCTACCCATCATTGCCTTGGTTTAAAAAAAAAAAAAAAAAAAAAAAAAAAA |
| 42 | AACCCGGCTACCCATCATTGCCTTGG |
| 44 | cggtctgttaggtcaggagttaaatctgg |
| 45 | gttaggtcaggagttaaatctgg |
| 46 | ggtcaggagttaaatctgg |
| 47 | cggtctgttaggtcaggagtt |
| 48 | ggtcaggagtt |
| 43 | CTTTCAGCAGGGACGAGGCCGCAAGGTGACGGTACCTGCAGAAGAAGCCCCGGCTAACTACGTG<br>CCAGCAGCCGCGGTAATACGTAGGGGGCAAGCGTTATCCGGATTCATTGGGCGTAAAGCGCGCG<br>TAGGCGGTCTGTTAGGTCAGGAGTTAAATCTGGGGGCTCAACCCCTATCCGCTCCTGATA |
| 50 | CTTTCAGCAGGGACGAGGCCGCAAGGTGA |

Amplification and Detection of *A. vaginae* in the Presence of Pseudotarget

This example amplifies and detects *A. vaginae* target nucleic acids in the presence of a pseudotarget. The pseudotarget nucleic acid contains primer binding sites, but does not contain a probe binding site. Thus, the pseudotarget reduces the detection signal received from a sample containing *A. vaginae*. In a first set of experiments, *A. vaginae* lysates was serially diluted to provide 4.08E+8, 4.08E+7, 4.08E+6, 4.08E+5, 4.08E+4 and 0 cfu/ml. Target nucleic acids were separated from the sample medium using target capture oligomers (SEQ ID NOS:5 & 6). An amplification reaction was set up as is generally described herein, e.g., see Example 4. Amplification oligomers used were SEQ ID NO:2 and SEQ ID NO:3. The amplification reaction was a TMA reaction (see also e.g., APTIMA HPV Assay package insert, Gen-Probe Incorporated, San Diego, Calif.) and included one of the dilutions of *Atopobium* lysates, amplification oligomers SEQ ID NOS:2 & 3 but no pseudotarget. At the end of the amplification reaction a detection reaction was performed as described above. The detection probe was SEQ ID NO:4 and included an acridinium ester label and detection was performed using a luminometer (e.g., LEADER®, Gen-Probe Incorporated, San Diego, Calif.). Results are as follows in Table 8:

TABLE 8

Bacterial Vaginosis Assay with *Atopobium* as a Target

| Dilution | 0 Cfu/ml | 4.08E+08 cfu/ml | 4.08E+07 cfu/ml | 4.08E+06 cfu/ml | 4.08E+05 cfu/ml | 4.08E+04 cfu/ml |
|---|---|---|---|---|---|---|
| RLU1 | 1,257 | 5,572,314 | 4,723,033 | 2,731,692 | 294,033 | 25,810 |
| RLU2 | 1,353 | 5,489,311 | 5,230,899 | 2,618,192 | 593,129 | 29,800 |
| RLU3 | 1,166 | 5,137,086 | 5,226,230 | 3,110,696 | 319,963 | 22,652 |
| RLU4 | 1,290 | 5,302,303 | 5,159,338 | 4,306,087 | 220,512 | 18,717 |
| RLU5 | 1,129 | 5,317,745 | 5,176,755 | 2,423,377 | 442,825 | 16,183 |
| Average RLU | 1,239 | 5,363,752 | 5,103,251 | 3,038,009 | 374,092 | 22,632 |
| ±SD | 91 | 170,685 | 214,786 | 751,857 | 146,311 | 5,441 |

To reduce the sensitivity of the amplification and detection reaction, a second experiment was performed using a pseudotarget spiked into the amplification reaction. In this set of experiments 4.08E+7 cfu/ml concentration was used along with SEQ ID NOS:5 & 6 as target capture oligomers, SEQ ID NOS:2 & 3 as amplification oligomers, SEQ ID NO:4 as a detection probe and SEQ ID NO:26 as a pseudotarget. The pseudotarget was provided as a serial dilution from 1.00E-2 to 1.25E-5 fmol/ml (see Table 9 for concentrations), and each concentration was tested individually with captured target nucleic acid. This experiment was set up as is generally described herein and was run as a TMA reaction with detection taking place on a luminometer (e.g., LEADER®, Gen-Probe Incorporated, San Diego, Calif. Example 4 and APTIMA HPV package insert). Results are as follows in Table 9 parts 1 & 2:

TABLE 9

| (part 1): Pseudotarget titration with *A. vaginae* added into each amplification reaction | | | | | | | |
|---|---|---|---|---|---|---|---|
| A. vag conc PsT conc. | 0 cfu/ml 0 fmol/ml | 0 fmol/ml | 1.00E−02 | 5.00E−03 | 2.50E−03 | 1.25E−03 | 1.00E−03 |
| RLU1 | 730 | 2327247 | 20184 | 31709 | 40866 | 56846 | 76307 |
| RLU2 | 705 | 3442850 | 20286 | 33347 | 37128 | 59168 | 78227 |
| RLU3 | 812 | 2846665 | 19605 | 32859 | 15529 | 54168 | 72708 |
| RLU4 | 659 | 3166180 | 20414 | 31195 | 34808 | 52628 | 70042 |
| RLU5 | 720 | 2917624 | 25022 | 38145 | 38391 | 48607 | 68407 |
| Average RLU | 725 | 2940113 | 21102 | 33451 | 33344 | 54283 | 73138 |
| SD | 56 | 414938 | 2213 | 2762 | 10197 | 4044 | 4126 |

| (part 2): Pseudotarget titration with *A. vaginae* added into each amplification reaction | | | | | | | |
|---|---|---|---|---|---|---|---|
| A. vag conc PsT conc. | 5.00E−04 | 2.50E−04 | 1.25E−04 | 1.00E−04 | 5.00E−05 | 2.50E−05 | 1.25E−05 |
| RLU1 | 75944 | 110381 | 149446 | 118530 | 254951 | 316581 | 363646 |
| RLU2 | 84378 | 99720 | 150423 | 183644 | 301574 | 281288 | 389686 |
| RLU3 | 86151 | 99341 | 163337 | 127318 | 216515 | 356124 | 476565 |
| RLU4 | 87987 | 113159 | 167748 | 187865 | 241695 | 321887 | 362172 |
| RLU5 | 72308 | 95711 | 149566 | 129400 | 204287 | 349987 | 352628 |
| Average RLU | 81354 | 103662 | 156104 | 149351 | 243804 | 325173 | 388939 |
| SD | 6842 | 7628 | 8764 | 33514 | 37988 | 29934 | 50876 |

These results show that the pseudotarget is effective in decreasing the sensitivity of an amplification reaction. Here, there is shown an inverse relationship between the concentration of pseudotarget in the sample and the RLU value.

Example 6

Direct Detection of *A. vaginae* in Samples Containing One or More Challenge Organisms This example uses the technique of nucleic acid hybridization to identify *A. vaginae* directly from a sample and without an amplification step. The sample can be a vaginal swab sample or other sample suspected of containing *A. vaginae*. *A. vaginae* is present in normal samples and in bacterial vaginosis samples, the difference being an increase in the *A. vaginae* present in a bacterial vaginosis sample. For this reason, a direct detection assay as described in this example can be used wherein the amplification step is omitted. Often, the increased *A. vaginae* is increased relative to and present with other flora in the sample. For this reason, the direct detection assay for detecting *A. vaginae* is often done in the presence of challenge organisms. Furthermore, detection of one of more of these challenge organisms can also be performed.

The method in this example will use a chemiluminescent, single stranded DNA probe that is complementary to the 16S ribosomal RNA or gene encoding the 16S rRNA of *A. vaginae*. When detecting more than one organism, the method uses two or more different chemiluminescent, single stranded DNA probes, each being complementary to a gene in its respective target organism. After the ribosomal RNA is released from the organism, the labeled DNA probe combines with it to form a stable DNA:RNA hybrid. The presence of stable DNA:RNA hybrids is detected in a luminometer by virtue of their chemiluminescent labels. For reference, U.S. Pat. Nos. 5,283,174, 5,656,207, 5,658,737 and 5,824,475 generally describe linear detection probes labeled with an AE compound for hybridizing to a target nucleic acid and detection by using a hybridization protection assay that selectively degrades the AE label in unhybridized probes and detects the signal from hybridized probes.

Probe oligomers used for the direct detection of *A. vaginae* will be antisense to the rRNA target nucleic acid. Table 10 illustrates some embodiments of probes useful for direct detection of a target nucleic acid. In Table 10, SEQ ID NOS:49 and 51-57 are the reverse complements of SEQ ID NOS:4, 14-18 and 33-34, respectively. In a further embodiment, the probes oligomers can optionally include one or more 2′-O-methoxy RNA residues. Additional embodiments of probe oligomers that can be used for direct detection of *A. vaginae* include those that are 10 to 40 nucleotides in length, are configured to specifically hybridize to a nucleotide sequence corresponding to nucleotides 538 to 566 of GenBank Accession No.: AF325325.1, gi:12240234 (SEQ ID NO:44) and are further configured antisense to the target rRNA.

TABLE 10

A. vaginae Direct Detection Probe Oligomer Sequences

| Sequence 5'→3' | SEQ ID NO. |
|---|---|
| CCUGUTTTUUCTCCTGUCC | 49 |
| TCACCTTGCGGCCTCGTCCCTGCTGA | 51 |
| CCAGATTTAACTCCTGACCTAAC | 52 |
| AACTCCTGACCTAACAGACCG | 53 |
| CCAGATTTAACTCCTGACC | 54 |
| GAGTATCCGGTATTAACCTCGG | 55 |
| TATCCCAGTGCAAAGGGCAGGTTGCC | 56 |
| TCCCGAGGCTATCCCAGTGCAAAGGGCA | 57 |

In this example, a sample suspected of containing *A. vaginae* can be directly detected. The sample is first processed under conditions that will release into solution the *A. vaginae* nucleic acids and the nucleic acids of any challenge organisms that are present. Direct detection of *A. vaginae* combines a labeled detection probe oligomer of SEQ ID NO:49 with the sample. Typically, the probe is present in solution at a total concentration of 0.1 pmol of probe in 0.1 ml of solution. The amount of probe used can be adjusted to provide a maximum detectable signal in an acceptable detection range, e.g., about 5,000,000 relative light units ("RLU"). The mixtures of probe and target sequences are then treated with a hybridization reagent to bind the probe to the target nucleic acid and then detect the chemiluminescent signal produced from hybridized probes substantially as described previously (U.S. Pat. Nos. 5,283,174 and 5,639,604, Arnold Jr. et al.). Briefly, the probe and target nucleic acid mixtures are incubated for about 20 min at 62.deg.C., then cooled at room temperature for about 5 min. Selection reagent is then added, mixed, and incubated for about 10 min at 62.deg.C. followed by room temperature for about 15 min to hydrolyze the label on unbound probes. Chemiluminescent signal will be produced from AE on bound probes by adding a first detection reagent, incubating the reaction, and then adding a second detection reagent. The signal can then be detected by measuring RLU by using a luminometer (e.g., LEADER®, Gen-Probe Incorporated, San Diego, Caif.), and the presence or absence of *A. vaginae* can be determined.

One or more organisms in addition to *A. vaginae* can also be directly detected from the sample. For example, a direct detection assay can be performed to detect *A. vaginae* and one or more of *G. vaginalis, Prevotella* sp, anaerobic gram positive cocci, *Mobiluncus* sp, *Mycoplasma hominis, Eggerthella hongkongensis, Megasphaera* sp, and *Leptotrichia sanguinegens*. Separate reaction can be set up for each of the organisms to be detected. The separate reactions can take place in different wells of a multi-well plate. A sample is processed under conditions that release the organisms' nucleic acids into solution. The released nucleic acids are then added to multiple wells of the multi-well plate. Separate probe solutions are prepared each to include a labeled detection probe targeting one of the organisms to be detected (e.g., a probe solution for *A. vaginae, G. vaginalis, Prevotella* sp, anaerobic gram positive cocci, *Mobiluncus* sp, *Mycoplasma hominis, Eggerthella hongkongensis, Megasphaera* sp, and/or *Leptotrichia sanguinegens*) and the probe solutions are added to separate reaction wells. The mixtures of probes and target sequences are then treated with a hybridization reagent to bind the probes to the target nucleic acids and then detect the chemiluminescent signal produced from hybridized probes substantially as described previously (U.S. Pat. Nos. 5,283,174 and 5,639,604, Arnold Jr. et al.). Briefly, the probe and target nucleic acid mixtures are incubated for about 20 min at 62.deg.C., then cooled at room temperature for about 5 min. Selection reagent is then added, mixed, and incubated for about 10 min at 62.deg.C. followed by room temperature for about 15 min to hydrolyze the label on unbound probes. Chemiluminescent signal will be produced from AE on bound probes by adding a first detection reagent, incubating the reaction, and then adding a second detection reagent. The signal can then be detected by measuring RLU by using a luminometer (e.g., LEADER®, Gen-Probe Incorporated, San Diego, Calif.), and the presence or absence of *A. vaginae, G. vaginalis, Prevotella* sp, anaerobic gram positive cocci, *Mobiluncus* sp, *Mycoplasma hominis, Eggerthella hongkongensis, Megasphaera* sp, and/or *Leptotrichia sanguinegens* can be determined.

The contents of the articles, patents, and patent applications are hereby incorporated by reference in their entirety to the same extent as if each individual publication was specifically and individually indicated as being incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

The invention claimed is:

1. A composition comprising at least two amplification oligomers for amplifying a 16S rRNA of *A. vaginae* or a gene encoding 16S rRNA of *A. vaginae*, wherein said amplification oligomers are configured to specifically hybridize to said 16S rRNA of *A. vaginae* or a gene encoding 16S rRNA of *A. vaginae* and generate an amplicon comprising a nucleotide sequence that is SEQ ID NO:43, wherein at least one of the amplification oligomers comprises a target-specific sequence selected from the group consisting of SEQ ID NO:2 and SEQ ID NO:27, and wherein at least one of the amplification oligomers comprises a 5' promoter sequence, and
wherein the composition further comprises a detection probe oligomer comprising (i) a nucleotide sequence of from 10 nucleotides in length to 40 nucleotides in length configured to specifically hybridize to all or a portion of a region of a target sequence of an *A. vaginae* 16S rRNA nucleic acid or amplified nucleic acid sequence, said region corresponding to SEQ ID NO:44; and (ii) a label selected from a luminescent compound and a fluorophore.

2. The composition of claim 1, wherein a first oligomer member of the at least two amplification oligomers comprises the target-specific sequence of SEQ ID NO:2 and a second oligomer member of the at least two amplification oligomers comprises the target-specific sequence of SEQ ID NO:27.

3. The composition of claim 2, wherein the second oligomer member comprises the sequence of SEQ ID NO:3.

4. The composition of claim 1, wherein said promoter sequence is a T7 RNA polymerase promoter sequence.

5. The composition of claim 4, wherein said promoter sequence is SEQ ID NO:25.

6. The composition of claim 5, wherein at least one of the amplification oligomers comprises the sequence of SEQ ID NO:3.

7. The composition of claim 1, wherein the detection probe comprises a sequence selected from the group consisting of SEQ ID NO:4, SEQ ID NO:15, SEQ ID NO:16, and SEQ ID NO:17.

8. The composition of claim 1, wherein the label is a chemiluminescent label.

9. The composition of claim 1, wherein said region corresponds to SEQ ID NO:45.

10. The composition of claim 1, wherein said region corresponds to SEQ ID NO:46.

11. The composition of claim 1, wherein said detection probe oligomer is from 11 nucleotides in length to 29 nucleotides in length, contains a sequence corresponding to SEQ ID NO:48, and specifically hybridizes to all or a portion of a region of an *A. vaginae* nucleic acid or amplified nucleic acid sequence corresponding to SEQ ID NO:44.

12. The composition of claim 1, wherein the sequence of said detection probe oligomer is SEQ ID NO:4.

13. A kit comprising at least two amplification oligomers for amplifying a 16S rRNA of *A. vaginae* or a gene encoding 16S rRNA of *A. vaginae*, wherein said amplification oligomers are configured to specifically hybridize to said 16S rRNA of *A. vaginae* or a gene encoding 16S rRNA of *A. vaginae* and generate an amplicon comprising a nucleotide sequence that is SEQ ID NO:43, wherein at least one of the amplification oligomers comprises a target-specific sequence selected from the group consisting of SEQ ID NO:2 and SEQ ID NO:27, and wherein at least one of the amplification oligomers comprises a 5' promoter sequence, and
wherein the kit further comprises a detection probe oligomer comprising (i) a nucleotide sequence of from 10 nucleotides in length to 40 nucleotides in length configured to specifically hybridize to all or a portion of a region of a target sequence of an *A. vaginae* 16S rRNA nucleic acid or amplified nucleic acid sequence, said region corresponding to SEQ ID NO:44; and (ii) a label selected from a luminescent compound and a fluorophore.

14. The kit of claim 13, wherein a first oligomer member of the at least two amplification oligomers comprises the target-specific sequence of SEQ ID NO:2 and a second oligomer member of the at least two amplification oligomers comprises the target-specific sequence of SEQ ID NO:27.

15. The kit of claim 14, wherein the second oligomer member comprises the sequence of SEQ ID NO:3.

16. The kit of claim 13, wherein said promoter sequence is a T7 RNA polymerase promoter sequence.

17. The kit of claim 16, wherein said promoter sequence is SEQ ID NO:25.

18. The kit of claim 17, wherein at least one of the amplification oligomers comprises the sequence of SEQ ID NO:3.

* * * * *